United States Patent
Hammerle et al.

(10) Patent No.: US 10,204,211 B2
(45) Date of Patent: Feb. 12, 2019

(54) HEALTHCARE OPERATIONS WITH PASSIVE NETWORK MONITORING

(71) Applicant: ExtraHop Networks, Inc., Seattle, WA (US)

(72) Inventors: Eric Joseph Hammerle, Seattle, WA (US); Samuel Kanen Clement, Brentwood, TN (US); Terry William Shaver, Lynnwood, WA (US); Matthew Couper Cauthorn, Decatur, GA (US)

(73) Assignee: ExtraHop Networks, Inc., Seattle, WA (US)

( * ) Notice: Subject to any disclaimer, the term of this patent is extended or adjusted under 35 U.S.C. 154(b) by 0 days.

(21) Appl. No.: 15/014,932

(22) Filed: Feb. 3, 2016

(65) Prior Publication Data
US 2017/0220739 A1    Aug. 3, 2017

(51) Int. Cl.
G06F 19/00    (2018.01)
H04L 12/26    (2006.01)
(Continued)

(52) U.S. Cl.
CPC ........ G06F 19/321 (2013.01); H04L 41/0893 (2013.01); H04L 41/14 (2013.01);
(Continued)

(58) Field of Classification Search
CPC .... G06Q 50/22; G06Q 50/24; G06F 19/3418; G06F 19/345; G06F 19/322; G06F 19/327; G06F 3/048
See application file for complete search history.

(56) References Cited

U.S. PATENT DOCUMENTS 5,027,269 A    6/1991    Grant
5,430,727 A    7/1995    Callon
(Continued)

OTHER PUBLICATIONS

Digital Imaging and Communications in Medicine (DICOM), Part 6: Data Dictionary. PS 3.6-2011. 2011. http://dicom.nema.org/Dicom/2011/11_06pu.pdf.*
(Continued)

*Primary Examiner* — Jonathan Durant
(74) *Attorney, Agent, or Firm* — John W. Branch; Lowe Graham Jones PLLC

(57) ABSTRACT

Embodiments are directed to monitoring communication over a network using a network monitoring computer (NMC). If one or more flows include healthcare traffic provided by one or more healthcare services, the NMC may perform further actions. Healthcare values from the one or more healthcare services may be provided from the network traffic. Values from one or more network traffic flows that are separate from the healthcare traffic may be provided. Other healthcare values from other flows may be provided that include healthcare traffic provided by the healthcare services. Accordingly, if a comparison of the healthcare values and the other healthcare values meet certain conditions, additional actions may be performed based on rules, or policies. The healthcare traffic may be compliant with one or more of Health Level Seven (HL7) standard, Digital Imaging and Communications in Medicine (DICOM) standard, or the like.

30 Claims, 11 Drawing Sheets

(51) Int. Cl.
    *H04L 12/851*    (2013.01)
    *H04L 12/24*     (2006.01)
    *G16H 80/00*     (2018.01)

(52) U.S. Cl.
    CPC ............ *H04L 43/062* (2013.01); *H04L 43/12*
            (2013.01); *H04L 47/2441* (2013.01); *G16H*
                                        *80/00* (2018.01)

(56) References Cited

U.S. PATENT DOCUMENTS

| | | | |
|---|---|---|---|
| 5,541,995 | A | 7/1996 | Normile et al. |
| 5,715,464 | A | 2/1998 | Crump et al. |
| 5,787,237 | A | 7/1998 | Reilly |
| 5,802,599 | A | 9/1998 | Cabrera et al. |
| 5,835,726 | A | 11/1998 | Shwed et al. |
| 5,857,188 | A | 1/1999 | Douglas |
| 5,928,363 | A | 7/1999 | Ruvolo |
| 6,141,686 | A | 10/2000 | Jackowski et al. |
| 6,263,049 | B1 | 7/2001 | Kuhn |
| 6,321,338 | B1 | 11/2001 | Porras et al. |
| 6,385,729 | B1 | 5/2002 | DiGiorgio et al. |
| 6,405,250 | B1 | 6/2002 | Lin et al. |
| 6,412,000 | B1 | 6/2002 | Riddle et al. |
| 6,526,044 | B1 | 2/2003 | Cookmeyer, II et al. |
| 6,560,636 | B2 | 5/2003 | Cohen et al. |
| 6,704,311 | B1 | 3/2004 | Chuah et al. |
| 6,704,874 | B1 | 3/2004 | Porras et al. |
| 6,765,909 | B1 | 7/2004 | Sen et al. |
| 6,807,156 | B1 | 10/2004 | Veres et al. |
| 6,807,565 | B1 | 10/2004 | Dodrill et al. |
| 6,883,015 | B1 | 4/2005 | Geen et al. |
| 6,901,517 | B1 | 5/2005 | Redmore |
| 6,944,599 | B1 | 9/2005 | Vogel et al. |
| 6,999,729 | B2 | 2/2006 | Wandel |
| 7,042,888 | B2 | 5/2006 | Berggreen |
| 7,089,326 | B2 | 8/2006 | Boucher et al. |
| 7,133,365 | B2 | 11/2006 | Klinker et al. |
| 7,143,153 | B1 | 11/2006 | Black et al. |
| 7,177,930 | B1 | 2/2007 | LoPresti |
| 7,181,769 | B1 | 2/2007 | Keanini et al. |
| 7,193,968 | B1 | 3/2007 | Kapoor et al. |
| 7,474,654 | B2 | 1/2009 | Guru |
| 7,480,292 | B2 | 1/2009 | Busi et al. |
| 7,535,906 | B2 | 5/2009 | Engbersen et al. |
| 7,545,499 | B2 | 6/2009 | Overbeck et al. |
| 7,580,356 | B1 | 8/2009 | Mishra et al. |
| 7,594,273 | B2 | 9/2009 | Keanini et al. |
| 7,602,731 | B2 | 10/2009 | Jain |
| 7,606,706 | B1 | 10/2009 | Rubin et al. |
| 7,609,630 | B2 | 10/2009 | Gobeil |
| 7,639,613 | B1 | 12/2009 | Ghannadian et al. |
| 7,644,150 | B1 | 1/2010 | Nucci et al. |
| 7,660,883 | B2 | 2/2010 | Fowlow |
| 7,774,456 | B1 | 8/2010 | Lownsbrough et al. |
| 7,864,764 | B1 | 1/2011 | Ma et al. |
| 7,916,652 | B1 | 3/2011 | Lima et al. |
| 7,979,555 | B2 | 7/2011 | Rothstein et al. |
| 8,040,798 | B2 | 10/2011 | Chandra et al. |
| 8,079,083 | B1 | 12/2011 | Bennett et al. |
| 8,125,908 | B2 | 2/2012 | Rothstein et al. |
| 8,185,953 | B2 | 5/2012 | Rothstein et al. |
| 8,411,677 | B1 | 4/2013 | Colloff |
| 8,555,383 | B1 * | 10/2013 | Marshall ................ H04L 69/22 713/151 |
| 8,619,579 | B1 | 12/2013 | Rothstein et al. |
| 9,191,400 | B1 | 11/2015 | Ptasinski et al. |
| 9,426,036 | B1 | 8/2016 | Roy |
| 9,692,658 | B2 | 6/2017 | Guo et al. |
| 10,038,611 | B1 | 7/2018 | Wu et al. |
| 10,063,434 | B1 | 8/2018 | Khanal et al. |
| 2002/0023080 | A1 | 2/2002 | Uga et al. |
| 2002/0024964 | A1 | 2/2002 | Baum et al. |
| 2002/0035604 | A1 | 3/2002 | Cohen et al. |
| 2002/0055998 | A1 | 5/2002 | Riddle et al. |
| 2002/0065912 | A1 | 5/2002 | Catchpole et al. |
| 2002/0078382 | A1 | 6/2002 | Sheikh et al. |
| 2002/0080720 | A1 | 6/2002 | Pegrum et al. |
| 2002/0091844 | A1 | 7/2002 | Craft et al. |
| 2002/0107953 | A1 | 8/2002 | Ontiveros et al. |
| 2002/0133586 | A1 | 9/2002 | Shanklin et al. |
| 2002/0152209 | A1 | 10/2002 | Merugu et al. |
| 2002/0156880 | A1 | 10/2002 | Mokuya |
| 2003/0093514 | A1 | 5/2003 | Valdes et al. |
| 2003/0131116 | A1 | 7/2003 | Jain et al. |
| 2003/0135667 | A1 | 7/2003 | Mann et al. |
| 2003/0149887 | A1 | 8/2003 | Yadav |
| 2003/0152094 | A1 | 8/2003 | Colavito et al. |
| 2003/0204621 | A1 | 10/2003 | Poletto et al. |
| 2003/0212900 | A1 | 11/2003 | Liu et al. |
| 2003/0214913 | A1 | 11/2003 | Kan et al. |
| 2003/0233361 | A1 | 12/2003 | Cady |
| 2004/0003094 | A1 | 1/2004 | See |
| 2004/0047325 | A1 | 3/2004 | Hameleers et al. |
| 2004/0088557 | A1 | 5/2004 | Malcolm et al. |
| 2004/0093414 | A1 | 5/2004 | Orton |
| 2004/0093513 | A1 | 5/2004 | Cantrell et al. |
| 2004/0146006 | A1 | 7/2004 | Jackson |
| 2004/0162070 | A1 | 8/2004 | Baral et al. |
| 2004/0199630 | A1 | 10/2004 | Sarkissian et al. |
| 2004/0250059 | A1 | 12/2004 | Ramelson et al. |
| 2005/0015455 | A1 | 1/2005 | Liu |
| 2005/0060427 | A1 | 3/2005 | Phillips et al. |
| 2005/0066196 | A1 | 3/2005 | Yagi |
| 2005/0086255 | A1 | 4/2005 | Schran et al. |
| 2005/0091341 | A1 | 4/2005 | Knight et al. |
| 2005/0091357 | A1 | 4/2005 | Krantz et al. |
| 2005/0100000 | A1 | 5/2005 | Faulkner et al. |
| 2005/0125553 | A1 | 6/2005 | Wu et al. |
| 2005/0182833 | A1 | 8/2005 | Duffie et al. |
| 2005/0201363 | A1 | 9/2005 | Gilchrist et al. |
| 2005/0210242 | A1 | 9/2005 | Troxel et al. |
| 2005/0234920 | A1 | 10/2005 | Rhodes |
| 2005/0251009 | A1 | 11/2005 | Morita et al. |
| 2005/0262237 | A1 | 11/2005 | Fulton et al. |
| 2006/0029096 | A1 | 2/2006 | Babbar et al. |
| 2006/0045016 | A1 | 3/2006 | Dawdy et al. |
| 2006/0045017 | A1 | 3/2006 | Yamasaki |
| 2006/0085526 | A1 | 4/2006 | Gulland |
| 2006/0106743 | A1 | 5/2006 | Horvitz et al. |
| 2006/0123477 | A1 | 6/2006 | Raghavan et al. |
| 2006/0174343 | A1 | 8/2006 | Duthie et al. |
| 2006/0184535 | A1 | 8/2006 | Kaluskar et al. |
| 2006/0230456 | A1 | 10/2006 | Nagabhushan et al. |
| 2007/0039051 | A1 | 2/2007 | Duthie et al. |
| 2007/0067641 | A1 | 3/2007 | Yegneswaran et al. |
| 2007/0077931 | A1 | 4/2007 | Glinka |
| 2007/0088845 | A1 | 4/2007 | Memon et al. |
| 2007/0143852 | A1 | 6/2007 | Keanini et al. |
| 2007/0153689 | A1 | 7/2007 | Strub et al. |
| 2007/0156886 | A1 | 7/2007 | Srivastava |
| 2007/0156919 | A1 | 7/2007 | Potti et al. |
| 2007/0157306 | A1 | 7/2007 | Elrod et al. |
| 2007/0192863 | A1 | 8/2007 | Kapoor et al. |
| 2007/0239639 | A1 | 10/2007 | Loughmiller et al. |
| 2007/0245420 | A1 | 10/2007 | Yong et al. |
| 2007/0256122 | A1 | 11/2007 | Foo et al. |
| 2008/0022401 | A1 | 1/2008 | Cameron et al. |
| 2008/0031141 | A1 | 2/2008 | Lean et al. |
| 2008/0034424 | A1 | 2/2008 | Overcash et al. |
| 2008/0034425 | A1 | 2/2008 | Overcash et al. |
| 2008/0059582 | A1 | 3/2008 | Hartikainen et al. |
| 2008/0062995 | A1 | 3/2008 | Kaas |
| 2008/0069002 | A1 | 3/2008 | Savoor et al. |
| 2008/0130659 | A1 | 6/2008 | Polland |
| 2008/0141275 | A1 | 6/2008 | Borgendale et al. |
| 2008/0147818 | A1 | 6/2008 | Sabo |
| 2008/0212586 | A1 | 9/2008 | Wang et al. |
| 2008/0219261 | A1 | 9/2008 | Lin et al. |
| 2008/0222717 | A1 | 9/2008 | Rothstein et al. |
| 2008/0232359 | A1 | 9/2008 | Kim et al. |
| 2009/0010259 | A1 | 1/2009 | Sirotkin |
| 2009/0034426 | A1 | 2/2009 | Luft et al. |
| 2009/0063665 | A1 | 3/2009 | Bagepalli et al. |

(56) References Cited

U.S. PATENT DOCUMENTS

| | | | |
|---|---|---|---|
| 2009/0168657 A1 | 7/2009 | Puri et al. | |
| 2009/0225675 A1 | 9/2009 | Baum et al. | |
| 2009/0228330 A1* | 9/2009 | Karras | G06Q 10/00 705/7.41 |
| 2009/0245083 A1 | 10/2009 | Hamzeh | |
| 2009/0268605 A1 | 10/2009 | Campbell et al. | |
| 2009/0292954 A1 | 11/2009 | Jiang et al. | |
| 2009/0296593 A1 | 12/2009 | Prescott | |
| 2010/0091770 A1 | 4/2010 | Ishikawa | |
| 2010/0095367 A1 | 4/2010 | Narayanaswamy | |
| 2010/0250928 A1 | 9/2010 | Goto | |
| 2010/0299158 A1* | 11/2010 | Siegel | G06F 19/3456 705/3 |
| 2010/0316216 A1 | 12/2010 | Fukushima et al. | |
| 2010/0322248 A1 | 12/2010 | Ivanov | |
| 2011/0019574 A1 | 1/2011 | Malomsoky et al. | |
| 2011/0073490 A1 | 3/2011 | Hayamizu et al. | |
| 2011/0126259 A1* | 5/2011 | Krishnamurthi | H04L 43/026 726/1 |
| 2011/0173441 A1 | 7/2011 | Bagepalli et al. | |
| 2011/0280149 A1 | 11/2011 | Okada et al. | |
| 2011/0320394 A1 | 12/2011 | McKeown et al. | |
| 2012/0130745 A1* | 5/2012 | Jones | G06Q 50/24 705/3 |
| 2012/0166962 A1* | 6/2012 | Lunsford | G06F 19/321 715/738 |
| 2012/0176917 A1 | 7/2012 | Matityahu et al. | |
| 2012/0215328 A1 | 8/2012 | Schmelzer | |
| 2012/0233694 A1 | 9/2012 | Baliga et al. | |
| 2012/0243533 A1 | 9/2012 | Leong | |
| 2012/0294305 A1 | 11/2012 | Rose et al. | |
| 2013/0010608 A1 | 1/2013 | Ramachandran et al. | |
| 2013/0042323 A1 | 2/2013 | Narayanaswamy | |
| 2013/0064084 A1 | 3/2013 | Babbar et al. | |
| 2013/0103734 A1 | 4/2013 | Boldyrev et al. | |
| 2013/0166730 A1 | 6/2013 | Wilkinson | |
| 2013/0176842 A1 | 7/2013 | Bauchot et al. | |
| 2013/0232104 A1 | 9/2013 | Goyal et al. | |
| 2013/0305357 A1 | 11/2013 | Ayyagari et al. | |
| 2014/0040451 A1 | 2/2014 | Agrawal et al. | |
| 2014/0077956 A1* | 3/2014 | Sampath | A61B 5/0022 340/573.1 |
| 2014/0142972 A1 | 5/2014 | Hosenfeld, Jr. | |
| 2014/0164584 A1 | 6/2014 | Joe et al. | |
| 2014/0222998 A1 | 8/2014 | Vasseur et al. | |
| 2014/0223325 A1 | 8/2014 | Melendez et al. | |
| 2014/0304211 A1 | 10/2014 | Horvitz | |
| 2015/0134554 A1 | 5/2015 | Clais et al. | |
| 2015/0199613 A1 | 7/2015 | Ruiz et al. | |
| 2015/0249512 A1 | 9/2015 | Adimatyam et al. | |
| 2015/0331771 A1 | 11/2015 | Conway | |
| 2016/0028755 A1 | 1/2016 | Vasseur et al. | |
| 2016/0036647 A1 | 2/2016 | Gonzalez et al. | |
| 2016/0055335 A1 | 2/2016 | Herwono et al. | |
| 2016/0182274 A1 | 6/2016 | Kiesekamp et al. | |
| 2016/0219066 A1 | 7/2016 | Vasseur et al. | |
| 2016/0359872 A1 | 12/2016 | Yadav et al. | |
| 2017/0279838 A1 | 9/2017 | Dasgupta et al. | |
| 2017/0288974 A1 | 10/2017 | Yoshihira et al. | |
| 2017/0310703 A1 | 10/2017 | Ackerman et al. | |
| 2018/0084011 A1 | 3/2018 | Joseph et al. | |
| 2018/0109507 A1 | 4/2018 | Caldera et al. | |
| 2018/0109557 A1 | 4/2018 | Yoo et al. | |
| 2018/0219879 A1 | 8/2018 | Pierce | |

OTHER PUBLICATIONS

Health Level Seven, Version 2.6, Appendix A. Nov. 2007. https://www.hl7.org/special/committees/vocab/V26_Appendix_A.pdf.*
Official Communication for U.S. Appl. No. 12/326,672 dated Jun. 9, 2010 (9 pages).
Official Communication for U.S. Appl. No. 12/326,672 dated Dec. 23, 2010 (15 pages).
Official Communication for U.S. Appl. No. 12/326,672 dated Jun. 22, 2011 (16 pages).
Official Communication for U.S. Appl. No. 12/326,672 dated Oct. 24, 2011 (9 pages).
Lin, Mark, "An Overview of Session Hijacking at the Network and Application Levels," Jan. 18, 2005 (16 pages).
U.S. Appl. No. 11/683,643, entitled "Detecting Anomalous Network Application Behavior", by Jesse Abraham Rothstein and Arindum Mukerji, filed Mar. 8, 2007 (40 pages).
U.S. Appl. No. 11/679,356, entitled "Capture and Resumption of Network Application Sessions", by Jesse Abraham Rothstein and Arindum Mukerji, filed Feb. 27, 2007 (37 pages).
Official Communication for U.S. Appl. No. 11/683,643 dated Apr. 28, 2010 (35 pages).
Official Communication for U.S. Appl. No. 11/683,643 dated Oct. 14, 2010 (43 pages).
Official Communication for U.S. Appl. No. 11/683,643 dated Aug. 25, 2011 (43 pages).
Official Communication for U.S. Appl. No. 11/683,643 dated Jan. 23, 2012 (6 pages).
Official Communication for U.S. Appl. No. 13/831,626, dated Sep. 3, 2013, (17 pages).
Official Communication for U.S. Appl. No. 13/831,673 dated Sep. 30, 2013, (10 pages).
Official Communication for U.S. Appl. No. 13/831,673 dated Mar. 6, 2014, (12 pages).
Official Communication for U.S. Appl. No. 13/831.673 dated May 22, 2014, (5 pages).
Official Communication for U.S. Appl. No. 14/518,996 dated Nov. 20, 2014, (41 pages).
Official Communication for U.S. Appl. No. 13/831,908 dated Jun. 25, 2014, (15 pages).
Official Communication for U.S. Appl. No. 14/500.893 dated Nov. 20, 2014, (15 pages).
Official Communication for U.S. Appl. No. 13/831,908 dated Apr. 9, 2014, (3 pages).
Official Communication for U.S. Appl. No. 13/831,908 dated Aug. 9, 2013, (29 pages).
Official Communication for U.S. Appl. No. 13/831,908 dated Jan. 13, 2014, (31 pages).
Official Communication for U.S. Appl. No. 14/107,631 dated Dec. 30, 2014, (12 pages).
Handel et al. "Hiding Data in the OSI Network Model," Los Alamos, New Mexico, 1996, (16 pages).
Official Communication for U.S. Appl. No. 14/107,631 dated Feb. 20, 2014, (16 pages).
Official Communication for U.S. Appl. No. 14/107,631 dated Sep. 26, 2014, (14 pages).
Handley et al., "Network Intrusion Detection: Evasion, Traffic Normalization, and End-to-End Protocol Semantics," 2011, International Computer Science Institute, (17 pages).
Information Sciences Institute. "Internet Protocol Darpa Internet Program Protocol Specification," Sep. 1981, (36 pages).
Fuertes, "Evaluation of OSPF Extensions in MANET Routing," Paris, 2007, (192 pages).
Parsons, "Moving Across the Internet: Code-Bodies. Code-Corpses, and Network Architecture," May 9, 2010, (20 pages).
Zander et al., "Covert Channels and Countermeasures in Computer Network Protocols." Dec. 2007, (7 pages).
Official Communication for U.S. Appl. No. 14/500,893 dated Feb. 18, 2015, (11 pages).
Official Communication for U.S. Appl. No. 14/107,580 dated Mar. 6, 2014, (13 pages).
Official Communication for U.S. Appl. No. 14/107,580 dated Sep. 15. 2014, (15 pages).
Official Communication for U.S. Appl. No. 14/107,580 dated Mar. 17, 2015, (5 pages).
Official Communication for U.S. Appl. No. 11/679,356 dated Jun. 22, 2009, (21 pages).
Official Communication for U.S. Appl. No. 11/679,356 dated Dec. 11, 2009, (23 pages).
Official Communication for U.S. Appl. No. 11/679,356 dated Feb. 22, 2010, (3 pages).

(56) References Cited

OTHER PUBLICATIONS

Official Communication for U.S. Appl. No. 11/679,356 dated Sep. 9, 2010, (7 pages).
Official Communication for U.S. Appl. No. 11/679,356 dated Mar. 4, 2011, (15 pages).
Official Communication for U.S. Appl. No. 15/207,213 dated Oct. 25, 2016, 18 pages.
Official Communication for U.S. Appl. No. 15/207,213 dated May 8, 2017, (5 pages).
Official Communication for U.S. Appl. No. 15/207,213 dated Jun. 1, 2017, (24 pages).
Official Communication for U.S. Appl. No. 15/690,135 dated Jan. 18, 2018, (6 pages).
Official Communication for U.S. Appl. No. 15/690,135 dated May 22, 2018, pp. 1-7.
Official Communication for U.S. Appl. No. 15/984,197 dated Aug. 31, 2018, pp. 1-60.
Official Communication for U.S. Appl. No. 15/891,311 dated Sep. 24, 2018, pp. 1-16.
Official Communication for U.S. Appl. No. 16/048,939 dated Sep. 19, 2018, pp. 1-36.
Official Communication for U.S. Appl. No. 15/891,311 dated Apr. 23, 2018, pp. 1-44.
Official Communication for U.S. Appl. No. 15/892,327 dated Apr. 23, 2018, pp. 1-35.
Official Communication for U.S. Appl. No. 15/891,273 dated Jun. 19, 2018, pp. 1-23.
Office Communication for U.S. Appl. No. 15/690,135 dated May 22, 2018, pp. 1-7.
Official Communication for U.S. Appl. No. 16/113,442 dated Nov. 6, 2018, pp. 1-41.
Official Communication for U.S. Appl. No. 16/100,116 dated Nov. 15, 2018, pp. 1-41.

\* cited by examiner

HEALTHCARE OPERATIONS WITH PASSIVE NETWORK MONITORING

TECHNICAL FIELD

The present invention relates generally to network monitoring, and more particularly, but not exclusively, to monitoring network traffic in a healthcare environment.

BACKGROUND

On most computer networks, bits of data arranged in bytes are packaged into collections of bytes called packets. These packets are generally communicated between computing devices over networks in a wired and/or wireless manner. A suite of communication protocols is typically employed to communicate between at least two endpoints over one or more networks. The protocols are typically layered on top of one another to form a protocol stack. One model for a network communication protocol stack is the Open Systems Interconnection (OSI) model, which defines seven layers of different protocols that cooperatively enable communication over a network. The OSI model layers are arranged in the following order: Physical (1), Data Link (2), Network (3), Transport (4), Session (5), Presentation (6), and Application (7).

Another model for a network communication protocol stack is the Internet Protocol (IP) model, which is also known as the Transmission Control Protocol/Internet Protocol (TCP/IP) model. The TCP/IP model is similar to the OSI model except that it defines four layers instead of seven. The TCP/IP model's four layers for network communication protocol are arranged in the following order: Link (1), Internet (2), Transport (3), and Application (4). To reduce the number of layers from four to seven, the TCP/IP model collapses the OSI model's Application, Presentation, and Session layers into its Application layer. Also, the OSI's Physical layer is either assumed or is collapsed into the TCP/IP model's Link layer. Although some communication protocols may be listed at different numbered or named layers of the TCP/IP model versus the OSI model, both of these models describe stacks that include basically the same protocols. For example, the TCP protocol is listed on the fourth layer of the OSI model and on the third layer of the TCP/IP model. To assess and troubleshoot communicated packets and protocols over a network, different types of network monitors can be employed. One type of network monitor, a "packet sniffer" may be employed to generally monitor and record packets of data as they are communicated over a network. Some packet sniffers can display data included in each packet and provide statistics regarding a monitored stream of packets. Also, some types of network monitors are referred to as "protocol analyzers" in part because they can provide additional analysis of monitored and recorded packets regarding a type of network, communication protocol, or application.

Generally, packet sniffers and protocol analyzers passively monitor network traffic without participating in the communication protocols. In some instances, they receive a copy of each packet on a particular network segment or VLAN from one or more members of the network segment. They may receive these packet copies through a port mirror on a managed Ethernet switch, e.g., a Switched Port Analyzer (SPAN) port, or a Roving Analysis Port (RAP). Port mirroring enables analysis and debugging of network communications. Port mirroring can be performed for inbound or outbound traffic (or both) on single or multiple interfaces.

In other instances, packet copies may be provided to the network monitors from a specialized network tap or from a software agent running on the client or server. In virtual environments, port mirroring may be performed on a virtual switch that is incorporated within the hypervisor.

In some instances, a proxy is actively arranged between two endpoints, such as a client device and a server device. The proxy intercepts each packet sent by each endpoint and optionally transforms and forwards the payload to the other endpoint. Proxies often enable a variety of additional services such as load balancing, caching, content filtering, and access control. In some instances, the proxy may operate as a network monitor. In other instances, the proxy may forward a copy of the packets to a separate network monitor.

Furthermore, as information technology infrastructure becomes more complex and more dynamic, it may be more difficult to determine and monitor which devices and applications may be operative on a network. Also, the complexity may make it difficult, especially in large networks, for determining dependencies among the network devices and applications that are operative on the networks. Accordingly, certain operating environments, such as healthcare environments may include disparate services that are communicating over the networks. Determining correlations or other information from the communication of the disparate devices may be difficult. Thus, it is with respect to these considerations and others that the present invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Description of Various Embodiments, which is to be read in association with the accompanying drawings, wherein.

DETAILED DESCRIPTION OF THE INVENTION

Figure 1:
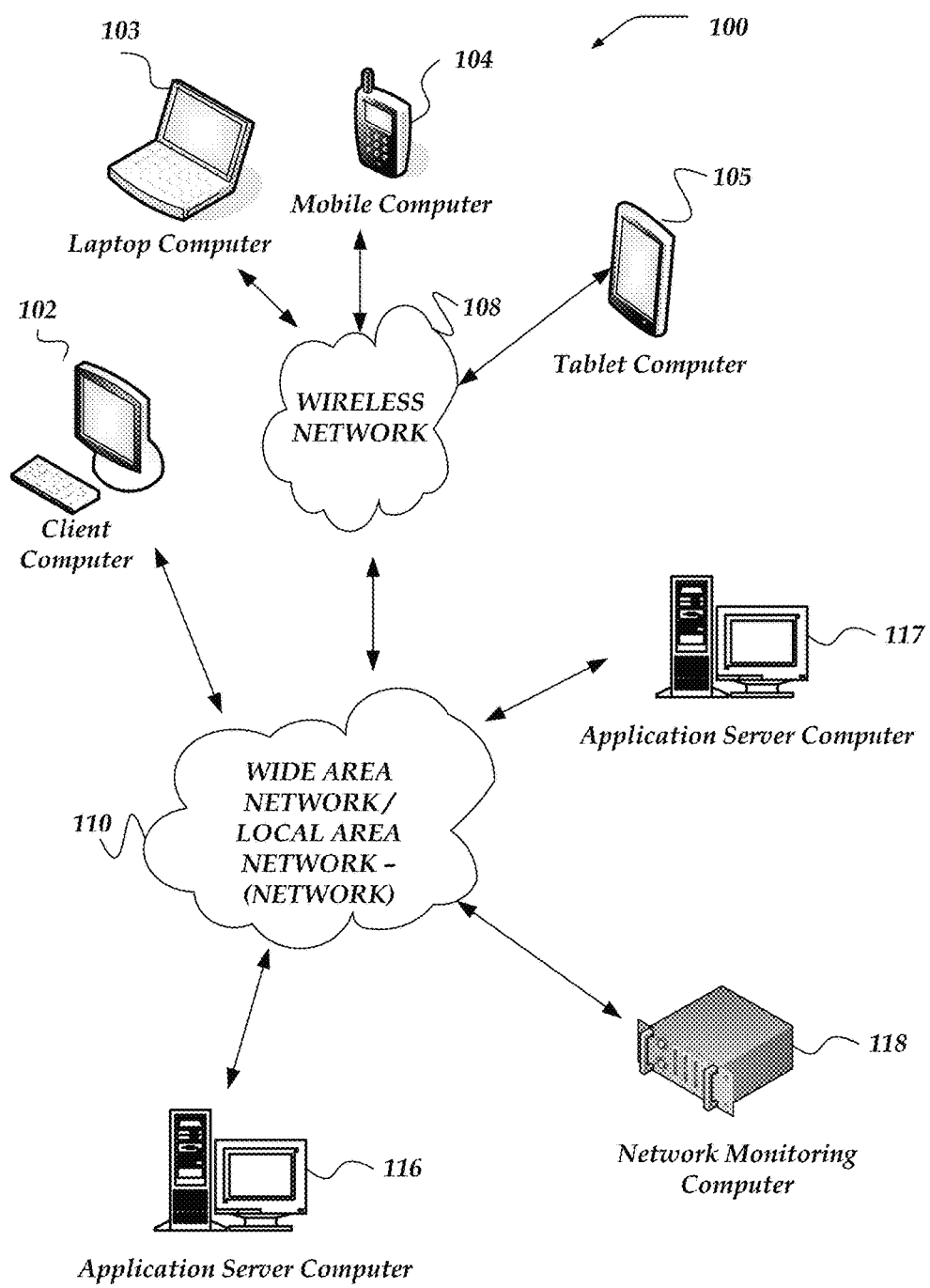
FIG. 1 illustrates a system environment in which various embodiments may be implemented.

Various embodiments now will be described more fully hereinafter with reference to the accompanying drawings, which form a part hereof, and which show, by way of illustration, specific exemplary embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media or devices. Accordingly, the various embodiments may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

For example embodiments, the following terms are also used herein according to the corresponding meaning, unless the context clearly dictates otherwise.

As used herein, the term "session" refers to a semi-permanent interactive packet interchange between two or more communicating endpoints, such as network devices. A session is set up or established at a certain point in time, and torn down at a later point in time. An established communication session may involve more than one message in each direction. A session may have stateful communication where at least one of the communicating network devices saves information about the session history to be able to communicate. A session may also provide stateless communication, where the communication consists of independent requests with responses between the endpoints. An established session is the basic requirement to perform a connection-oriented communication. A session also is the basic step to transmit in connectionless communication modes.

As used herein, the terms "network connection," and "connection" refer to communication sessions with a semi-permanent connection for interactive packet interchange between two or more communicating endpoints, such as network devices. The connection may be established before application data is transferred, and where a stream of data is delivered in the same or different order than it was sent. The alternative to connection-oriented transmission is connectionless communication. For example, the datagram mode of communication used by the Internet Protocol (IP) and the Universal Datagram Protocol (UDP) may deliver packets out of order, since different packets may be routed independently and could be delivered over different paths. Packets associated with a TCP protocol connection may also be routed independently and could be delivered over different paths. However, for TCP connections the network communication system may provide the packets to application endpoints in the correct order.

Connection-oriented communication may be a packet-mode virtual circuit connection. For example, a transport layer virtual circuit protocol such as the TCP protocol can deliver packets of data in order although the lower layer switching is connectionless. A connection-oriented transport layer protocol such as TCP can also provide connection-oriented communications over connectionless communication. For example, if TCP is based on a connectionless network layer protocol (such as IP), this TCP/IP protocol can then achieve in-order delivery of a byte stream of data, by means of segment sequence numbering on the sender side, packet buffering and data packet reordering on the receiver side. Alternatively, the virtual circuit connection may be established in a datalink layer or network layer switching mode, where all data packets belonging to the same traffic stream are delivered over the same path, and traffic flows are identified by some connection identifier rather than by complete routing information, which enables fast hardware based switching.

As used herein, the terms "session flow" and "network flow" refer to one or more network packets or a stream of network packets that are communicated in a session that is established between at least two endpoints, such as two network devices. In at least one of the various embodiments, flows may be useful if one or more of the endpoints of a session may be behind a network traffic management device, such as a firewall, switch, router, load balancer, or the like. In at least one of the various embodiments, such flows may be used to ensure that the packets sent between the endpoints of a flow may be routed appropriately.

Typically, establishing a TCP based connection between endpoints begins with the execution of an initialization protocol and creates a single bi-directional flow between two endpoints, e.g., one direction of flow going from endpoint A to endpoint B, the other direction of the flow going from endpoint B to endpoint A, where each endpoint is at least identified by an IP address and a TCP port. In at least one of the various embodiments, a tuple may be employed to identify a flow. Also, other protocols may establish a separate flow for control information that enables management of at least one or more flows between two or more endpoints.

As used herein, the terms "network monitor", "network monitoring computer", or "NMC" refer to an application (software, hardware, or some combination) that is arranged to monitor and record flows of packets in a session that are communicated between at least two endpoints over at least one network. The NMC can provide information for assessing different aspects of these monitored flows. In at least one embodiment, the NMC passively monitors network packet traffic without participating in the communication protocols. This monitoring is performed for a variety of reasons, including troubleshooting and proactive remediation, end-user experience monitoring, SLA monitoring, capacity planning, application lifecycle management, infrastructure change management, infrastructure optimization, business intelligence, security, and regulatory compliance. The NMC can receive network communication for monitoring through a variety of means including network taps, wireless receivers, port mirrors or directed tunnels from network switches, clients or servers including the endpoints themselves, or other infrastructure devices. In at least some of the various embodiments, the NMC may receive a copy of each packet on a particular network segment or virtual local area network (VLAN). Also, for at least some of the various embodiments, they may receive these packet copies through a port mirror on a managed Ethernet switch, e.g., a Switched Port Analyzer (SPAN) port, or a Roving Analysis Port (RAP). Port mirroring enables analysis and debugging of network communications. Port mirroring can be performed for inbound or outbound traffic (or both) on single or multiple interfaces.

The NMC may track network connections from and to end points such as a client and/or a server. The NMC may also extract information from the packets including protocol information at various layers of the communication protocol stack. The NMC may reassemble or reconstruct the stream of data exchanged between the endpoints. The NMC may perform decryption of the payload at various layers of the protocol stack. The NMC may passively monitor the network traffic or it may participate in the protocols as a proxy. The NMC may attempt to classify the network traffic according to communication protocols that are used.

The NMC may also perform one or more actions for classifying protocols that may be a necessary precondition for application classification. While some protocols run on well-known ports, others do not. Thus, even if there is traffic on a well-known port, it is not necessarily the protocol generally understood to be assigned to that port. As a result, the NMC may perform protocol classification using one or more techniques, such as, signature matching, statistical analysis, traffic analysis, and other heuristics. In some cases, the NMC may use adaptive protocol classification techniques where information used to classify the protocols may be accumulated and/or applied over time to further classify the observed protocols. The NMC may categorize the traffic where categories might include file transfers, streaming audio, streaming video, database access, interactive, gaming, and the like. The NMC may attempt to determine whether the traffic corresponds to known communications protocols, such as HTTP, FTP, SMTP, RTP, TDS, TCP, IP, and the like.

As used herein, the term "healthcare service" refers to a computer based application that provides one or more services used in a healthcare setting or healthcare facility. Healthcare settings/facilities may include clinics, hospitals, medical labs, pharmacies, or the like, or combination thereof. Healthcare services may include applications for patient admission, record keeping, insurance processing, medical imaging, laboratory management/operations, scheduling, electronic medical records, digital medical charts, messaging, pharmacy operations, or the like, or combination thereof.

As used herein, the term "healthcare environment" refers to a networked computing environment that includes one or more healthcare services. Some or all of the healthcare services in a healthcare environment may be coupled over one or more networks. In some cases, one or more healthcare services may be operating independently from one or more other healthcare services.

As used herein, the terms "healthcare traffic," "healthcare network traffic," or "healthcare communications" refer to network communications related to the operations of and/or interactions of various healthcare services in a healthcare environment. In some embodiments, healthcare traffic may comprise one or more complex network protocols that may be specifically designed for healthcare applications. This enables disparate healthcare services to use a common interface for sharing healthcare information, such as, patient information, diagnosis information, lab results, medical insurance information, scheduling, inventory, provider orders, or the like, or combination thereof. For example, network traffic that comprises protocols built on the Health Level Seven (HL7) standard may be considered healthcare traffic. In some case, other network traffic may be considered healthcare traffic depending on the services/application that are providing the communications.

As used herein, the terms "patient values" refers to values from healthcare traffic that are associated with a particular patient. Patient values may include, disease information for a patient, a patient's diagnosis, a payment, patient appointments/schedules, a patient's provider schedule, lab results for a patient, patient identification information (e.g., name, birthday, or the like), duration of patient visits, or the like.

The following briefly describes embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed to monitoring communication over a network using a network monitoring computer (NMC) that may be enabled to monitor flows of packets over a network such that one or more processors in a network computer may perform various actions. In at least one of the various embodiments, if one or more flows include healthcare traffic provided by one or more healthcare services, the NMC may perform further actions. In at least one of the various embodiments, one or more healthcare values from the one or more healthcare services may be provided from the network traffic. In at least one of the various embodiments, one or more values from one or more network traffic flows that are separate from the healthcare traffic may be provided.

In at least one of the various embodiments, one or more other healthcare values from one or more other flows may be provided that include healthcare traffic provided by the one or more healthcare services. Accordingly, in at least one of the various embodiments, if a comparison of the one or more healthcare values and the one or more other healthcare values meet one or more conditions, additional actions may be performed. In some cases, one or more actions may be provided from one or more rules, or policies. And, in at least one of the various embodiments, the one or more actions may be performed by the NMC and the result of the one or more actions may be communicated to one or more other network computers. In some embodiment, the one or more actions may include providing one or more notifications to one or more users.

In at least one of the various embodiments, the healthcare traffic may be compliant with one or more of Health Level Seven (HL7) standard, Digital Imaging and Communications in Medicine (DICOM) standard, or the like, or combination thereof.

In at least one of the various embodiments, if a comparison of the one or more healthcare values and the one or more other values meet one or more conditions, still further actions may be performed. In at least one of the various embodiments, one or more actions using one or more rules policies may be provided. And in at least one of the various embodiments, the one or more actions may be performed by the NMC such that a result of the one or more actions may be communicated to one or more other network computers.

In at least one of the various embodiments, actions may include, providing one or more patient values from the healthcare traffic that may be from the one or more healthcare services. And in some embodiments, actions may include providing trend information that may be associated with a disease, a diagnosis, a payment, patient schedules, provider schedules, lab results, duration of patient visits, or the like, or combination thereof.

In at least one of the various embodiments, the one or more conditions may include comparing one or more healthcare values in real-time with one or more defined values. Also, in at least one of the various embodiments, conditions may include comparing one or more healthcare transaction results in real-time with one or more defined values such that one or more incomplete healthcare transactions may be identified.

In at least one of the various embodiments, one or more records that include at least a portion of the healthcare traffic and the one or more healthcare values may be provided. In some embodiments, the one or more records may be stored in a data store. Accordingly, one or more reports based using one or more queries and the one or more records may be provided.

Illustrated Operating Environment

FIG. 1 shows components of one embodiment of an environment in which embodiments of the invention may be practiced. Not all of the components may be required to practice the invention, and variations in the arrangement and type of the components may be made without departing from the spirit or scope of the invention. As shown, system 100 of FIG. 1 includes local area networks (LANs)/wide area networks (WANs)—(network) 110, wireless network 108, client computers 102-105, Application Server Computer 116, Application Server Computer 117, Network monitoring computer 118, or the like.

At least one embodiment of client computers 102-105 is described in more detail below in conjunction with FIG. 2. In one embodiment, at least some of client computers 102-105 may operate over one or more wired and/or wireless networks, such as networks 108, and/or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to send requests and receive responses over the web. The browser application may be configured to receive and display graphics, text, multimedia, and the like, employing virtually any web-based language. In one embodiment, the browser application is enabled to employ JavaScript, HyperText Markup Language (HTML), eXtensible Markup Language (XML), JavaScript Object Notation (JSON), Cascading Style Sheets (CSS), or the like, or combination thereof, to display and send a message. In one embodiment, a user of the client computer may employ the browser application to perform various activities over a network (online). However, another application may also be used to perform various online activities.

Client computers 102-105 also may include at least one other client application that is configured to receive and/or send content between another computer. The client application may include a capability to send and/or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), a client certificate, or other device identifier. Such information may be provided in one or more network packets, or the like, sent between other client computers, application server computer 116, application server computer 117, network monitoring computer 118, or other computers.

Client computers 102-105 may further be configured to include a client application that enables an end-user to log into an end-user account that may be managed by another computer, such as application server computer 116, application server computer 117, network monitoring computer 118, or the like. Such an end-user account, in one non-limiting example, may be configured to enable the end-user to manage one or more online activities, including in one non-limiting example, project management, software development, system administration, configuration management, search activities, social networking activities, browse various websites, communicate with other users, or the like. Further, client computers may be arranged to enable users to provide configuration information, or the like, to network monitoring computer 118. Also, client computers may be arranged to enable users to display reports, interactive user-interfaces, and/or results provided by network monitor computer 118.

Wireless network 108 is configured to couple client computers 103-105 and its components with network 110. Wireless network 108 may include any of a variety of wireless sub-networks that may further overlay stand-alone ad-hoc networks, and the like, to provide an infrastructure-oriented connection for client computers 103-105. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile computers, such as client computers 103-105 with various degrees of mobility. In one non-limiting example, wireless network 108 may enable a radio connection through a radio network access such as Global System for Mobil communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 103-105 and another computer, network, a cloud-based network, a cloud instance, or the like.

Network 110 is configured to couple network computers with other computers, including, application server computer 116, application server computer 117, network monitoring computer 118, client computers 102-105 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, Ethernet port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, and/or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information of an Internet Protocol (IP).

Additionally, communication media typically embodies computer readable instructions, data structures, program modules, or other transport mechanism and includes any information non-transitory delivery media or transitory delivery media. By way of example, communication media includes wired media such as twisted pair, coaxial cable, fiber optics, wave guides, and other wired media and wireless media such as acoustic, RF, infrared, and other wireless media.

One embodiment of application server computer 116 and/or application server computer 117 is described in more detail below in conjunction with FIG. 3. Briefly, however, application server computer 116-117 includes virtually any network computer capable of hosting applications and/or providing services in network environment.

One embodiment of network monitoring computer 118 is described in more detail below in conjunction with FIG. 3. Briefly, however, network monitoring computer 118 includes virtually any network computer capable of passively monitoring communication traffic in a network environment.

Although FIG. 1 illustrates application server computer 116, application server computer 117, and network monitor device 118, each as a single computer, the innovations and/or embodiments are not so limited. For example, one or more functions of application server computers 116-117, and/or network monitoring computer 118, or the like, may be distributed across one or more distinct network computers. Moreover, in at least one embodiment, network monitoring computer 118 may be implemented using a plurality of network computers. Further, in at least one of the various embodiments, application server computers 116-117, and/or network monitoring computer 118 may be implemented using one or more cloud instances in one or more cloud networks. Accordingly, these innovations and embodiments are not to be construed as being limited to a single environment, and other configurations, and other architectures are also envisaged.

Illustrative Client Computer

Figure 2:
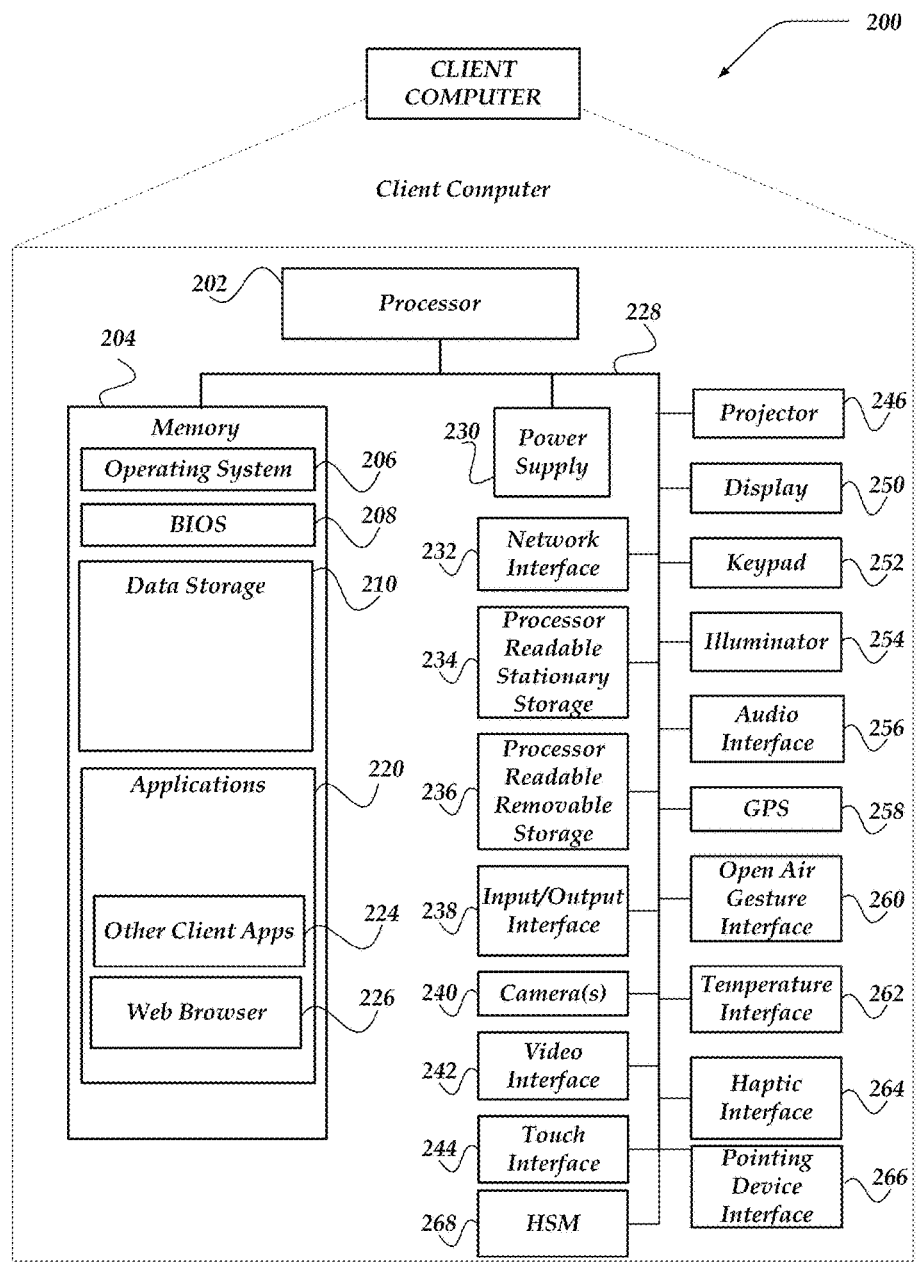
FIG. 2 illustrates a schematic embodiment of a client computer.

FIG. 2 shows one embodiment of client computer 200 that may include many more or less components than those shown. Client computer 200 may represent, for example, at least one embodiment of mobile computers or client computers shown in FIG. 1.

Client computer 200 may include processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Client computer 200 may optionally communicate with a base station (not shown), or directly with another computer. And in one embodiment, although not shown, a gyroscope may be employed within client computer 200 to measuring and/or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements and/or recharges the battery.

Network interface 232 includes circuitry for coupling client computer 200 to one or more networks, and is constructed for use with one or more communication protocols and technologies including, but not limited to, protocols and technologies that implement any portion of the OSI model for mobile communication (GSM), CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (MC).

Audio interface 256 may be arranged to produce and receive audio signals such as the sound of a human voice. For example, audio interface 256 may be coupled to a speaker and microphone (not shown) to enable telecommunication with others and/or generate an audio acknowledgement for some action. A microphone in audio interface 256 can also be used for input to or control of client computer 200, e.g., using voice recognition, detecting touch based on sound, and the like.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch and/or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication and/or provide light. Illuminator 254 may remain active for specific periods of time or in response to event messages. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing and/or using security/cryptographic information such as, keys, digital certificates, passwords, passphrases, two-factor authentication information, or the like. In some embodiments, hardware security module may be employed to support one or more standard public key infrastructures (PKI), and may be employed to generate, manage, and/or store keys pairs, or the like. In some embodiments, HSM 268 may be a stand-alone computer, in other cases, HSM 268 may be arranged as a hardware card that may be added to a client computer.

Client computer 200 may also comprise input/output interface 238 for communicating with external peripheral devices or other computers such as other client computers and network computers. The peripheral devices may include an audio headset, virtual reality headsets, display screen glasses, remote speaker system, remote speaker and microphone system, and the like. Input/output interface 238 can utilize one or more technologies, such as Universal Serial Bus (USB), Infrared, WiFi, WiMax, Bluetooth™, and the like.

Input/output interface 238 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect and/or measure data that is external to client computer 200.

Haptic interface 264 may be arranged to provide tactile feedback to a user of the client computer. For example, the haptic interface 264 may be employed to vibrate client computer 200 in a particular way when another user of a computer is calling. Temperature interface 262 may be used to provide a temperature measurement input and/or a temperature changing output to a user of client computer 200. Open air gesture interface 260 may sense physical gestures of a user of client computer 200, for example, by using single or stereo video cameras, radar, a gyroscopic sensor inside a computer held or worn by the user, or the like. Camera 240 may be used to track physical eye movements of a user of client computer 200.

GPS transceiver 258 can determine the physical coordinates of client computer 200 on the surface of the Earth, which typically outputs a location as latitude and longitude values. GPS transceiver 258 can also employ other geo-positioning mechanisms, including, but not limited to, tri-angulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 258 can determine a physical location for client computer 200. In at least one embodiment, however, client computer 200 may, through other components, provide other information that may be employed to determine a physical location of the client computer, including for example, a Media Access Control (MAC) address, IP address, and the like.

Human interface components can be peripheral devices that are physically separate from client computer 200, allowing for remote input and/or output to client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™ and the like. One non-limiting example of a client computer with such peripheral human interface components is a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that is configured to receive and to send web pages, web-based messages, graphics, text, multimedia, and the like. The client computer's browser application may employ virtually any programming language, including a wireless application protocol messages (WAP), and the like. In at least one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

Memory 204 may include RAM, ROM, and/or other types of memory. Memory 204 illustrates an example of computer-readable storage media (devices) for storage of information such as computer-readable instructions, data structures, program modules or other data. Memory 204 may store BIOS 208 for controlling low-level operation of client computer 200. The memory may also store operating system 206 for controlling the operation of client computer 200. It will be appreciated that this component may include a general-purpose operating system such as a version of UNIX, or LINUX™, or a specialized client computer communication operating system such as Windows Phone™, or the Symbian® operating system. The operating system may include, or interface with a Java virtual machine module that enables control of hardware components and/or operating system operations via Java application programs.

Memory 204 may further include one or more data storage 210, which can be utilized by client computer 200 to store, among other things, applications 220 and/or other data. For example, data storage 210 may also be employed to store information that describes various capabilities of client computer 200. The information may then be provided to another device or computer based on any of a variety of methods, including being sent as part of a header during a communication, sent upon request, or the like. Data storage 210 may also be employed to store social networking information including address books, buddy lists, aliases, user profile information, or the like. Data storage 210 may further include program code, data, algorithms, and the like, for use by a processor, such as processor 202 to execute and perform actions. In one embodiment, at least some of data storage 210 might also be stored on another component of client computer 200, including, but not limited to, non-transitory processor-readable removable storage device 236, processor-readable stationary storage device 234, or even external to the client computer.

Applications 220 may include computer executable instructions which, when executed by client computer 200, transmit, receive, and/or otherwise process instructions and data. Applications 220 may include, for example, other client applications 224, web browser 226, or the like. Client computers may be arranged to exchange communications, such as, queries, searches, messages, notification messages, event messages, alerts, performance metrics, log data, API calls, or the like, combination thereof, with application servers and/or network monitoring computers.

Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Additionally, in one or more embodiments (not shown in the figures), client computer 200 may include an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), client computer 200 may include a hardware microcontroller instead of a CPU. In at least one embodiment, the microcontroller may directly execute its own embedded logic to perform actions and access its own internal memory and its own external Input and Output Interfaces (e.g., hardware pins and/or wireless transceivers) to perform actions, such as System On a Chip (SOC), or the like.

Illustrative Network Computer

Figure 3:
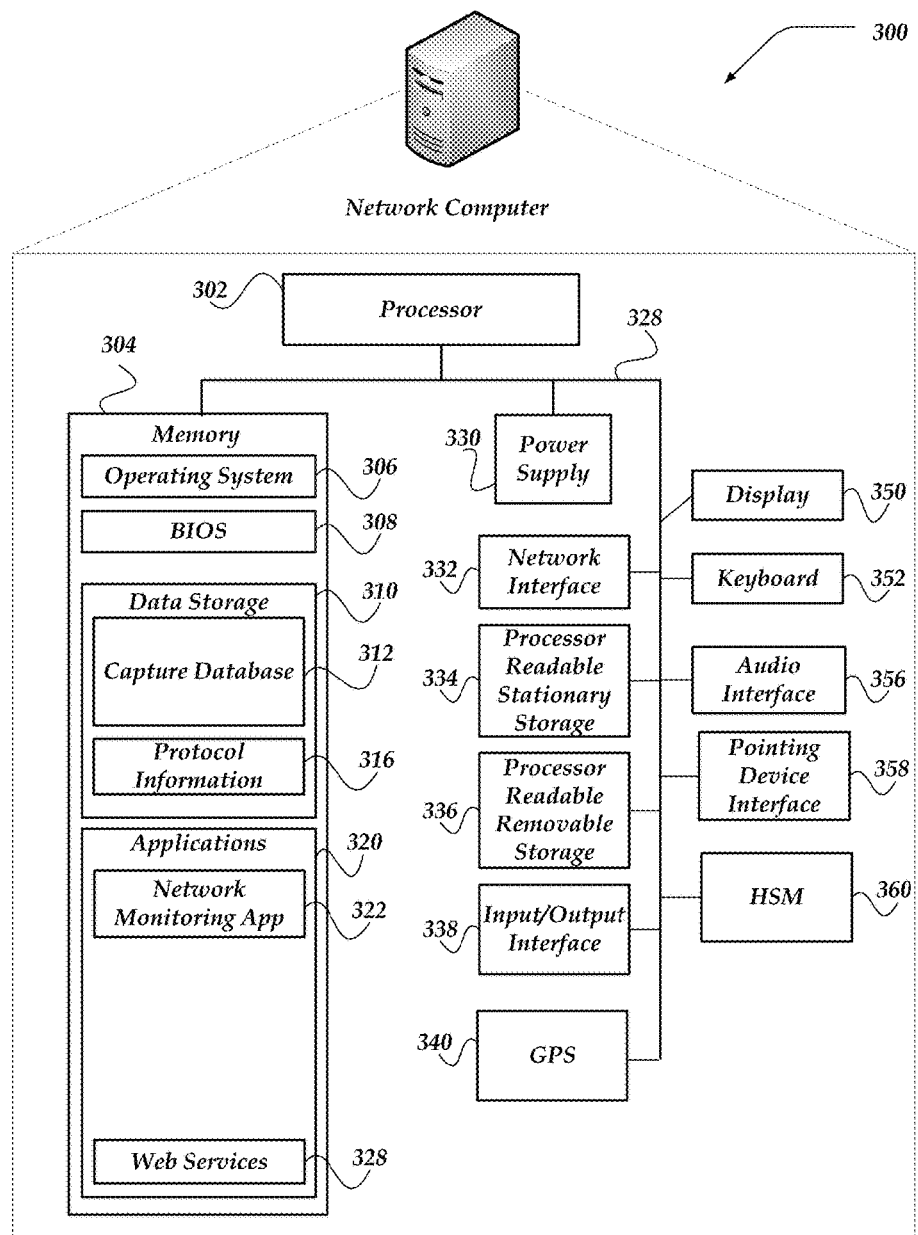
FIG. 3 illustrates a schematic embodiment of a network computer.

FIG. 3 shows one embodiment of network computer 300 that may be included in a system implementing at least one of the various embodiments. Network computer 300 may include many more or less components than those shown in FIG. 3. However, the components shown are sufficient to disclose an illustrative embodiment for practicing these innovations. Network computer 300 may represent, for example, one embodiment of at least one of application server computers 116-117, network monitoring computer 118 of FIG. 1.

As shown in the figure, network computer 300 includes a processor 302 that may be in communication with a memory 304 via a bus 328. In some embodiments, processor 302 may be comprised of one or more hardware processors, or one or more processor cores. In some cases, one or more of the one or more processors may be specialized processors designed to perform one or more specialized actions, such as, those described herein. Network computer 300 also includes a power supply 330, network interface 332, audio interface 356, display 350, keyboard 352, input/output interface 338, processor-readable stationary storage device 334, and processor-readable removable storage device 336. Power supply 330 provides power to network computer 300.

Network interface 332 includes circuitry for coupling network computer 300 to one or more networks, and is constructed for use with one or more communication protocols and technologies including, but not limited to, protocols and technologies that implement any portion of the Open Systems Interconnection model (OSI model), global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra wide band (UWB), IEEE 802.16 Worldwide Interoperability for Microwave Access (WiMax), Session Initiation Protocol/Real-time Transport Protocol (SIP/RTP), or any of a variety of other wired and wireless communication protocols. Network interface 332 is sometimes known as a transceiver, transceiving device, or network interface card (NIC). Network computer 300 may optionally communicate with a base station (not shown), or directly with another computer.

Audio interface 356 is arranged to produce and receive audio signals such as the sound of a human voice. For example, audio interface 356 may be coupled to a speaker and microphone (not shown) to enable telecommunication with others and/or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED) or any other type of light reflective or light transmissive display that can be used with a computer. Display 350 may be a handheld projector or pico projector capable of projecting an image on a wall or other object.

Network computer 300 may also comprise input/output interface 338 for communicating with external devices or computers not shown in FIG. 3. Input/output interface 338 can utilize one or more wired or wireless communication technologies, such as USB™, Firewire™, WiFi, WiMax, Thunderbolt™, Infrared, Bluetooth™, Zigbee™, serial port, parallel port, and the like.

Also, input/output interface 338 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect and/or measure data that is external to network computer 300. Human interface components can be physically separate from network computer 300, allowing for remote input and/or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices such as mice, styluses, track balls, or the like, may communicate through pointing device interface 358 to receive user input.

GPS transceiver 340 can determine the physical coordinates of network computer 300 on the surface of the Earth, which typically outputs a location as latitude and longitude values. GPS transceiver 340 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 340 can determine a physical location for network computer 300. In at least one embodiment, however, network computer 300 may, through other components, provide other information that may be employed to determine a physical location of the client computer, including for example, a Media Access Control (MAC) address, IP address, and the like.

Memory 304 may include Random Access Memory (RAM), Read-Only Memory (ROM), and/or other types of memory. Memory 304 illustrates an example of computer-readable storage media (devices) for storage of information such as computer-readable instructions, data structures, program modules or other data. Memory 304 stores a basic input/output system (BIOS) 308 for controlling low-level operation of network computer 300. The memory also stores an operating system 306 for controlling the operation of network computer 300. It will be appreciated that this component may include a general-purpose operating system such as a version of UNIX, or LINUX™, or a specialized operating system such as Microsoft Corporation's Windows® operating system, or the Apple Corporation's IOS® operating system. The operating system may include, or interface with a Java virtual machine module that enables control of hardware components and/or operating system operations via Java application programs. Likewise, other runtime environments may be included.

Memory 304 may further include one or more data storage 310, which can be utilized by network computer 300 to store, among other things, applications 320 and/or other data. For example, data storage 310 may also be employed to store information that describes various capabilities of network computer 300. The information may then be provided to another device or computer based on any of a variety of methods, including being sent as part of a header during a communication, sent upon request, or the like. Data storage 410 may also be employed to store social networking information including address books, buddy lists, aliases, user profile information, or the like. Data storage 310 may further include program code, data, algorithms, and the like, for use by a processor, such as processor 302 to execute and perform actions such as those actions described below. In one embodiment, at least some of data storage 310 might also be stored on another component of network computer 300, including, but not limited to, non-transitory media inside processor-readable removable storage device 336, processor-readable stationary storage device 334, or any other computer-readable storage device within network computer 300, or even external to network computer 300. Data storage 310 may include, for example, capture database 312, protocol information 316, or the like. Capture database 312 may be a data store that contains one or more records, logs, events, or the like, produced during monitoring of the networks. Protocol information 316 may contain various rules and/or configuration information related to one or more network communication protocols (e.g., HL7) that may be employed, or the like.

Applications 320 may include computer executable instructions which, when executed by network computer 300, transmit, receive, and/or otherwise process messages (e.g., SMS, Multimedia Messaging Service (MIMS), Instant Message (IM), email, and/or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth. Applications 320 may include network monitoring application 322 that perform actions further described below. In at least one of the various embodiments, one or more of the applications may be implemented as modules and/or components of another application. Further, in at least one of the various embodiments, applications may be implemented as operating system extensions, modules, plugins, or the like.

Furthermore, in at least one of the various embodiments, network monitoring application 322 may be operative in a cloud-based computing environment. In at least one of the various embodiments, these applications, and others, that comprise the management platform may be executing within virtual machines and/or virtual servers that may be managed in a cloud-based based computing environment. In at least one of the various embodiments, in this context the applications may flow from one physical network computer within the cloud-based environment to another depending on performance and scaling considerations automatically managed by the cloud computing environment. Likewise, in at least one of the various embodiments, virtual machines and/or virtual servers dedicated to network monitoring application 322 may be provisioned and de-commissioned automatically.

Also, in at least one of the various embodiments, network monitoring application 322, or the like, may be located in virtual servers running in a cloud-based computing environment rather than being tied to one or more specific physical network computers.

Further, network computer 300 may also comprise hardware security module (HSM) 360 for providing additional tamper resistant safeguards for generating, storing and/or using security/cryptographic information such as, keys, digital certificates, passwords, passphrases, two-factor authentication information, or the like. In some embodiments, hardware security module may be employ to support one or more standard public key infrastructures (PKI), and may be employed to generate, manage, and/or store keys pairs, or the like. In some embodiments, HSM 360 may be a stand-alone network computer, in other cases, HSM 360 may be arranged as a hardware card that may be installed in a network computer.

Additionally, in one or more embodiments (not shown in the figures), the network computer may include an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), the network computer may include one or more hardware microcontrollers instead of a CPU. In at least one embodiment, the one or more microcontrollers may directly execute their own embedded logic to perform actions and access their own internal memory and their own external Input and Output Interfaces (e.g., hardware pins and/or wireless transceivers) to perform actions, such as System On a Chip (SOC), or the like.

Illustrative Logical System Architecture

Figure 4:
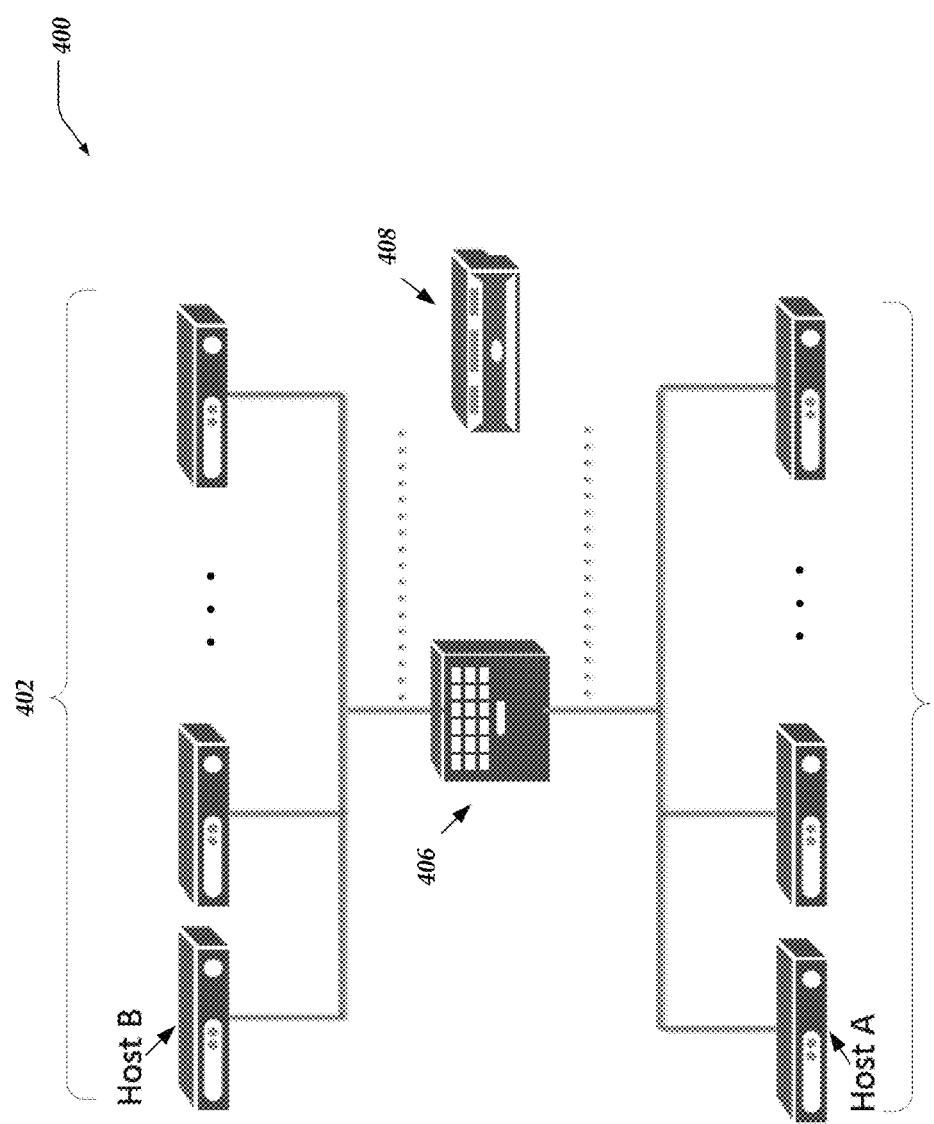
FIG. 4 illustrates a logical architecture of a system for improving healthcare operations with passive network monitoring in accordance with at least one of the various embodiments.

FIG. 4 illustrates a logical architecture of system 400 for improving healthcare operations with passive network monitoring in accordance with at least one of the various embodiments. System 400 may be arranged to include a plurality of network devices and/or network computers on first network 402 and a plurality of network devices and/or network computers on second network 404. Communication between the first network and the second network is managed by switch 406. Also, NMC 408 may be arranged to passively monitor and/or record packets (network packets) that are communicated in network connection flows between network devices and/or network computers on first network 402 and second network 404. For example, the communication of flows of packets between the Host B network computer and the Host A network computer are managed by switch 406 and NMC 408 may be passively monitoring and recording some or all of the network traffic comprising these flows.

Also, NMC 408 may be arranged to passively monitor network communication between and among hosts that are on the same network, such as, network computers 402.

NMC 408 may be arranged to receive network communication for monitoring through a variety of means including network taps, wireless receivers, port mirrors or directed tunnels from network switches, clients or servers including the endpoints themselves, or other infrastructure devices. In at least some of the various embodiments, the NMC may receive a copy of each packet on a particular network segment or virtual local area network (VLAN). Also, for at least some of the various embodiments, NMCs may receive these packet copies through a port mirror on a managed Ethernet switch, e.g., a Switched Port Analyzer (SPAN) port, or a Roving Analysis Port (RAP). Port mirroring enables analysis and debugging of network communications. Port mirroring can be performed for inbound or outbound traffic (or both) on single or multiple interfaces.

Figure 5:
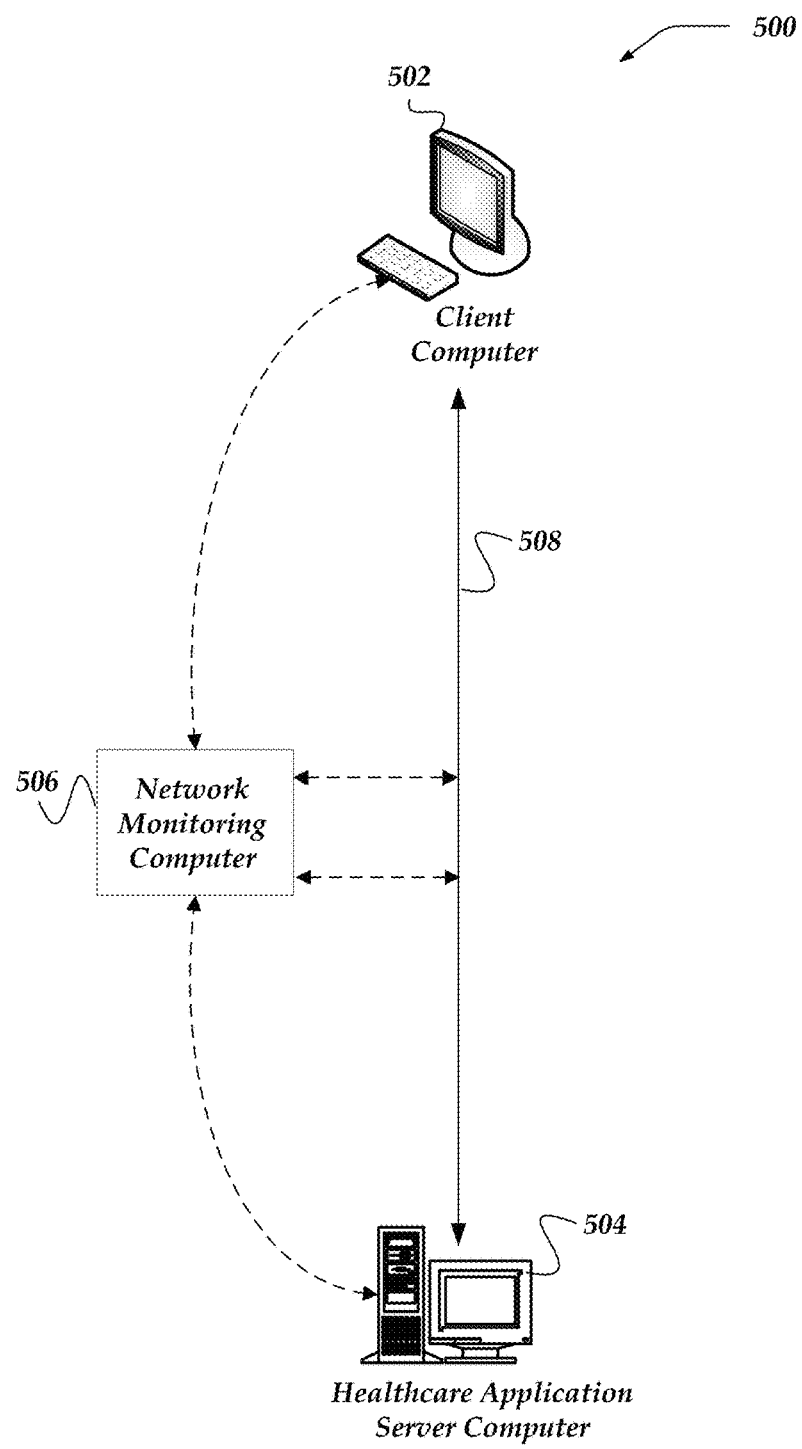
FIG. 5 illustrates a logical architecture of a system for improving healthcare operations with passive network monitoring in accordance with at least one of the various embodiments.

FIG. 5 illustrates a logical architecture of system 500 for improving healthcare operations with passive network monitoring in accordance with at least one of the various embodiments. A system, such as, system 500, may include one or more client computers, such as, client computer 502, one or more healthcare application server computers 504, and one or more network monitoring computers, such as, network monitoring computer (NMC) 506, each coupled over network 508, which may be similar to network 108 and/or network 110 in FIG. 1.

In at least one of the various embodiments, client computer 502 may be arranged to be executing one or more healthcare applications, such as, a digital patient record. Accordingly, as updates to the record are made, they may be communicated to one or more healthcare applications that may be executing on healthcare application server computer 504. In some embodiments, NMC 506 may be arranged to passively monitoring the network traffic that comprises the communications between client computer 502 and healthcare application server computer 504.

In at least one of the various embodiments, client computer 502 and healthcare application server computer 504 may be arranged to communication using one or more dedicated healthcare messaging/communication protocols, such as, HL7. Accordingly, NMC 506 may be arranged to monitor the communications and apply configuration information and/or policy rules based on context that may be derived from the interpreting the contents of the communications. In some cases, NMC 506 may be arranged communicate alerts, notification, log messages, or the like, to client computers, application server computers, network computers, or the like, depending in the contents of the communication occurring over the network. For example, the NMC 506 may be arranged to detect if one or more communications are successfully acknowledged. If an acknowledgment message is not observed, the NMC 506 may be arranged to provide an alert or notification so a user may take corrective actions as necessary.

In at least one of the various embodiments, the NMC 506 may provide real-time notification if communications between disparate applications in the healthcare environment indicate that there may be problems that require additional actions. In at least one of the various embodiments, NMC 506 may passively monitoring communications between multiple services in a healthcare environment.

Accordingly, NMC 506 may be arranged to correlate communications among the different applications to obtain context and/or perspective that may be unavailable to a single application or service. In some environments, one or more of the different healthcare applications may be unaware of the actions of one or more other healthcare applications. For example, while some application may be integrated to work together and/or share information, they may be other applications communicating on the one network that are not integrated, or otherwise have no visibility to some applications and/or services on the network.

In at least one of the various embodiments, NMC 506 may be arranged to perform various discovery actions that enable it to identify all of the services on a network. For example, passively collected network traffic may be used to determine hosts on the network as well as some or all of the roles performed by the discovered hosts.

Also, in at least one of the various embodiments, by observing the communication patterns, NMC 506 may determine relationships between the different services in the networking environment. For example, in a large healthcare enterprise there may be many services. In some case it may be difficult by observation to determine how the services are integrated or how they may be depend on each other. In some embodiments, if a NMC is connected to a network, it may passively monitor the network traffic. The NMC may be arranged to correlate the network traffic in transactions that may be used to determine which services are communicating with each other. In some cases, the NMC may identify services that are inadvertently sharing information. Likewise, the NMC monitoring may identify services that should be sharing information but they are not.

Also, in some embodiments, NMCs may be arranged to provide real-time auditing of various services. For example, the NMC may be configured to ensure that a defined workflow or treatment plan may be followed. In such an example, the NMC may capture network traffic that indicates that a patient has checked into a particular department/clinic of a hospital complex. When an order is entered indicating that the patient should visit another department (e.g., to get an x-ray, have blood drawn, pick up a prescription, or the like) the NMC may monitor traffic on the network to see messages indicating that the patient has checked into to the proper department. If a duration is exceeded before seeing confirmation of the patient's actions, a notification may be sent so corrective action may be taken.

Figure 6:
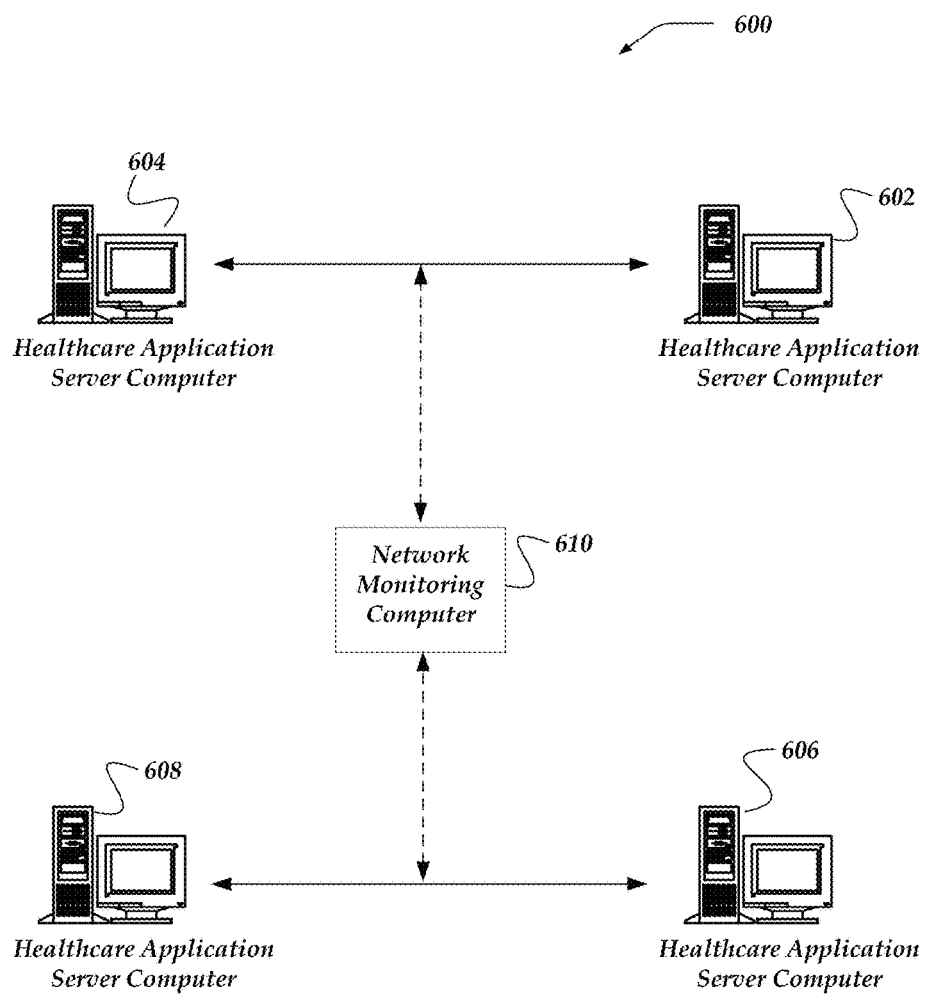
FIG. 6 illustrates a logical architecture of a system for improving healthcare operations with passive network monitoring in accordance with at least one of the various embodiments.

FIG. 6 illustrates a logical architecture of system 700 for improving healthcare operations with passive network monitoring in accordance with at least one of the various embodiments. As described above, various healthcare services may be communicating in a networked environment. In some embodiments, some or all for the healthcare services may be operating as independent separate systems. In some embodiments, one or more healthcare services may be arranged to communicate with some but not all healthcare services in the network environment.

In this example, healthcare application server computer (HASC) 602, HASC 604, HASC 606, or HASC 608 may be arranged to provide various healthcare services in a networked environment. For example, HASC 602 may be a patient scheduling/admission application, HASC 604 may be a healthcare billing/insurance system, HASC 606 may be a radiology department system, and HASC 608 may be pharmacy system. Each of these HASCs may be arranged to intercommunicate using one or more healthcare information protocols, such as, HL7, Digital Imaging and Communications in Medicine (DICOM), or the like, or combination thereof. Further, in some embodiments, HASCs may be generating various network traffic for other applications and/or services in the system, such as, user authentication (e.g., LDAP, Active Directory, or the like), email, VOIP, telnet, FTP, DNS, DHCP, or the like, or combination thereof.

In at least one of the various embodiments, a network monitoring computer (NMC), such as, NMC 610, may be arranged to passively monitor network traffic that is occurring on the network. Accordingly, in at least one of the various embodiments, NMC 610 may see network traffic from disparate systems that may not be communicating with each other, or otherwise communicatively integrated.

In at least one of the various embodiments, NMC 610 may be arranged to monitor one or more healthcare service transactions that may be occurring among the HASCs. In at least one of the various embodiments, NMC 610 may be arranged to identify in real-time various events and/or combinations of events that may trigger one or more actions to be performed. In this way NMC 610 may provide oversight over the performance of the HASCs in the network. Accordingly, in at least one of the various embodiments, NMC 610 may be arranged to apply one or more rules that enforce one or more rules or policies that may initiate the performance of one or more actions depending on various conditions. For example, in some embodiment, if HASC 602 sends HASC 604 an important HL7, but HASC 604 does not send an acknowledge message, NMC 610 may generate an alert separate from the HASCs communications. In some embodiments, NMC 610 may be configured to evaluate the communications between HASCs without requiring changes to the applications running on the HASCs. Thus, in some embodiments, policies may be enforced by NMC 610 without requiring expensive and/or modifications/integrations to the HASCs.

Further, in some embodiments, an NMC may be arranged to monitor network traffic and ensure that HASCs remain in compliance with one or more policies. For example, NMC 610 may be arranged to detect if a HASC is modified such that it is not including one or more required fields of information when communicating patient information to other HASCs.

Also, in at least one of the various embodiments, since NMC 610 may be monitoring other network traffic in addition to healthcare traffic (e.g., HL7). Accordingly, in some embodiments, NMC 610 may be arranged to determine one or more correlations between the healthcare traffic and the other network traffic. In some embodiments, an NMC may detect anomalies or potential issues by monitoring one or more of the other network traffic that may be separate from the healthcare traffic. For example, in some embodiments, a NMC may detect that a HASC has received and acknowledged a healthcare transaction but by monitoring a database network protocol, the NMC may determine if the target HSAC has failed to commit the transaction to stable storage in a database. Accordingly, in this example, the NMC may be enforcing a policy that confirms that the transactions are stored into a network database—additional actions may be performed.

In at least one of the various embodiments, more NMCs, HSACs, or the like, may be used in production environments. Also, in some embodiments, there may be additional, switches, routers, networks, computer, network appliances, or the like, included in a production healthcare environment. However, system 600 is at least sufficient to disclose the innovations included herein to one of ordinary skill in the art.

Figure 7:
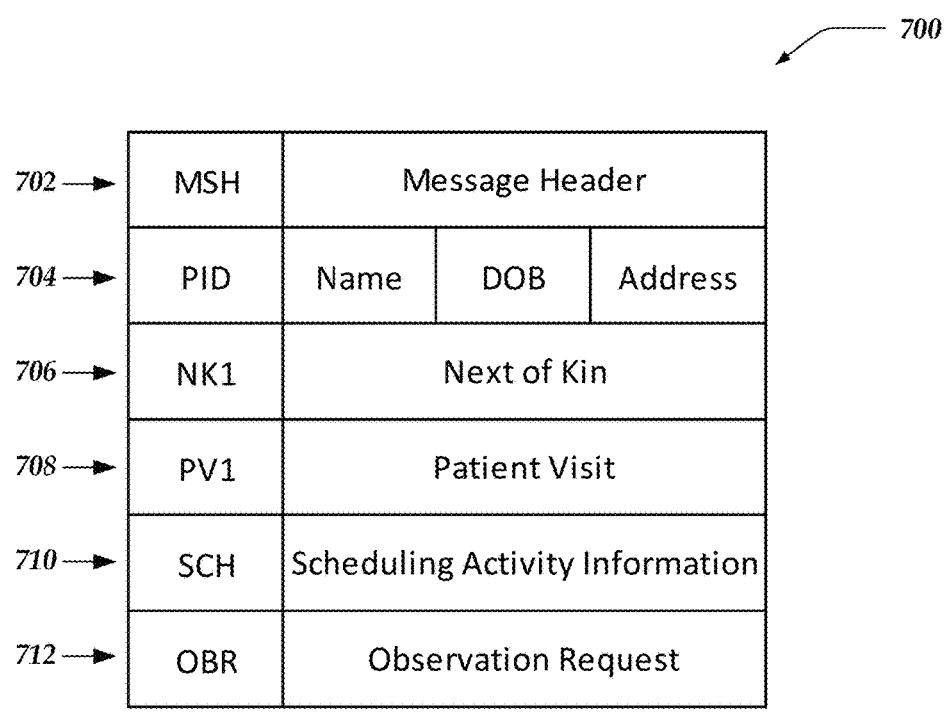
FIG. 7 illustrates a logical representation of a portion of a HL7 message in accordance with at least one of the various embodiments.

FIG. 7 illustrates a logical representation of a portion of HL7 message 700 in accordance with at least one of the various embodiments. Various messaging protocols and/or message standard may be employed for communicating information within a healthcare environment. In some embodiments, messages may use the HL7 standard. Message represents a very simplified example of the structure of a HL7 message. The data format for message 700 may depend on the implementation of the message passing system. Also, different versions of HL7 may support different data format options. For example, a message structure may be formatted using one or more defined delimiters, such as, carriage-return/line-feeds, pipes, carets, whitespace, or the like, combination thereof. In other cases, fixed width fields, extensible markup language (XML), JavaScript object notation (JSON), comma separated values, or the like, may be used to provide message structure.

In at least one of the embodiments, HL7 messages may be arranged to include one or more message segments each with one or more fields. In this example, message 700 include six message segments, including, message-header segment 702, patient-identification segment 704, next-of-kin message segment 706, patient-visit segment 708, scheduling-activity-information segment 710, and observation-request segment 712. In production systems HL7 messages may include far more message segments than shown here with segment having the potential of having many fields.

Also, in at least one of the various embodiments, the HL7 standards being used in a healthcare environment may be available and considered known. Accordingly, NMCs may be configured to recognize the various parts of an HL7 message. Thus, NMCs may monitor network traffic for the various values for message types, segments, fields, of the like.

Also, in at least one of the various embodiments, NMCs may be arranged to track the state and/or status of one or more transactions that may be occurring in the network. In some embodiments, NMCs may be arranged to generate one or more alerts or notifications if certain states and/or conditions are met. For example, if a patient is checked into a clinic or department, a HL7 message identifying the patient may be generated by the check-in service and communicated one or more other services, such as, a billing service. In this example, a NMC may monitor the HL7 messages which may include an indication that that patient requires a language interpreter. Accordingly, the NMC may be arranged to send a real-time notice that a specific interpreter may be required.

In at least one of the various embodiments, the NMC may be arranged to provide real-time notifications without having to modify the HL7 interfaces of the different services. The NMCs may passively monitor the network traffic and read the HL7 message directly from the network traffic rather than having to participate directly in the communication transactions.

Likewise, NMCs may be able to correlate HL7 messages from services that may not be arranged to communicate directly with each other. In such cases, the NMC may be arranged to passively monitor messages from non-integrated services and use information from both services to form correlations and provide conclusions.

Generalized Operations

FIGS. 8-11 represent the generalized operation for improving healthcare operations with passive network monitoring in accordance with at least one of the various embodiments. In at least one of the various embodiments, processes 800, 900, 1000, and 1100 described in conjunction with FIGS. 8-11 may be implemented by and/or executed by one or more processors on a single network computer (or network monitoring computer), such as network computer 300 of FIG. 3. In other embodiments, these processes, or portions thereof, may be implemented by and/or executed on a plurality of network computers, such as network computer 300 of FIG. 3. In yet other embodiments, these processes, or portions thereof, may be implemented by and/or executed on one or more virtualized computers, such as, those in a cloud-based environment. However, embodiments are not so limited and various combinations of network computers, client computers, or the like may be utilized. Further, in at least one of the various embodiments, the processes described in conjunction with FIGS. 8-11 may be used for improving healthcare operations with passive network monitoring in accordance with at least one of the various embodiments and/or architectures such as those described in conjunction with FIGS. 4-7. Further, in at least one of the various embodiments, some or all of the action performed by processes 800, 900, 1000, and 1100 may be executed in part by network monitoring application 322 running on one or more processors of one or more network computers.

Figure 8:
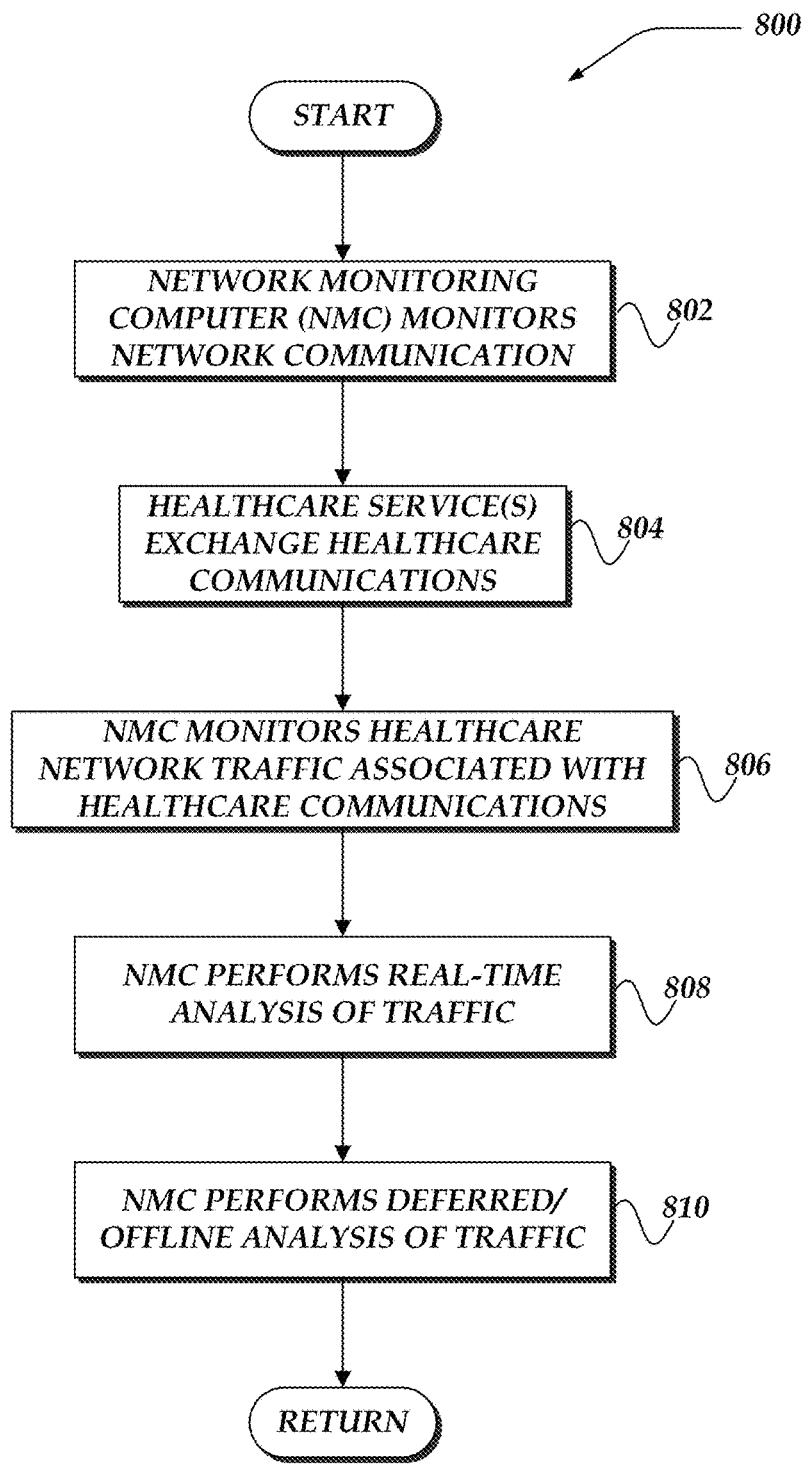
FIG. 8 illustrates an overview flowchart of a process for improving healthcare operations with passive network monitoring in accordance with at least one of the various embodiments.

FIG. 8 illustrates an overview flowchart of process 800 for improving healthcare operations with passive network monitoring in accordance with at least one of the various embodiments. After a start block, at block 802, in at least one of the various embodiments, a network monitoring computer (NMC) may be monitoring network traffic in a healthcare environment. In some embodiments, one or more NMCs may be arranged to monitor some or all of a network in a healthcare environment. In some cases, the healthcare environment may be a hospital complex, multi-care clinic, specialty clinic, or the like. In some embodiments, portions of a healthcare networking environment may be monitored while other portions of the network are not monitored.

In at least one of the various embodiments, the NMCs may be arranged to passively monitor some or all of the network traffic on monitored networks. Accordingly, the NMC may monitor the network traffic without integrating with the various services and systems using the network.

At block 804, in at least one of the various embodiments, one or more healthcare services may provide healthcare network traffic over a network. In some embodiments, two or more healthcare services may be exchanging one or more healthcare messages. In some embodiments, the various healthcare services may be communicating over the network using HL7. The actual messages communicated between the different healthcare services may depend on the particular operations and workflow of the healthcare environment. Likewise, in some embodiments, the contents of the messages may be arranged according the need of a particular healthcare environment. For example, while the healthcare communications may use a particular standard/protocol such as HL7, there may be considerable flexibility in how information may be represented within the protocol.

At block 806, in at least one of the various embodiments, the NMC may be arranged to monitor the healthcare network traffic provided by the one or more healthcare services. In at least one of the various embodiments, NMCs may be configured to monitor various kinds of network traffic. In some embodiments, configuration information that may include, filters, rules, conditions, or the like, may be used to select that type of network traffic that may be monitored by a NMC. Accordingly, in at least one of the various embodiments, configuration information may be arranged to enable the NMC to monitor some or all of the network traffic associated with the healthcare communications (e.g., healthcare traffic/healthcare network traffic).

In at least one of the various embodiments, NMCs may be arranged to simultaneously monitor healthcare communications and other network traffic, such as, emails, telnet sessions, database traffic, web server traffic, or the like, or combination thereof.

At block 808, in at least one of the various embodiments, the NMC may perform actions to provide real-time analysis of the healthcare traffic. In at least one of the various embodiments, the analysis may drive content for one or more real-time reports (e.g., dashboards). Also, in at least one of the various embodiments, the real-time analysis may be the generation of various performance/activity metrics that may be used for tracking operations in the healthcare environment.

In at least one of the various embodiments, there may be various actions associated with one or more conditions that may be met. Accordingly, in at least one of the various embodiments, if one or more defined conditions are met, the certain defined actions may be performed by the NMC.

At block 810, in at least one of the various embodiments, the NMC may be arranged to perform actions to provide deferred/offline analysis of the healthcare traffic. In at least one of the various embodiments, the NMC may be configured to store some or all of the monitored healthcare traffic. Accordingly, the collected data may be data mined to discover insights into the operations and/or performance of the healthcare environment. In some embodiments, data mining may be performed by third party data mining services that use the captured and stored healthcare information. Next, control may be return to a calling process.

Figure 9:
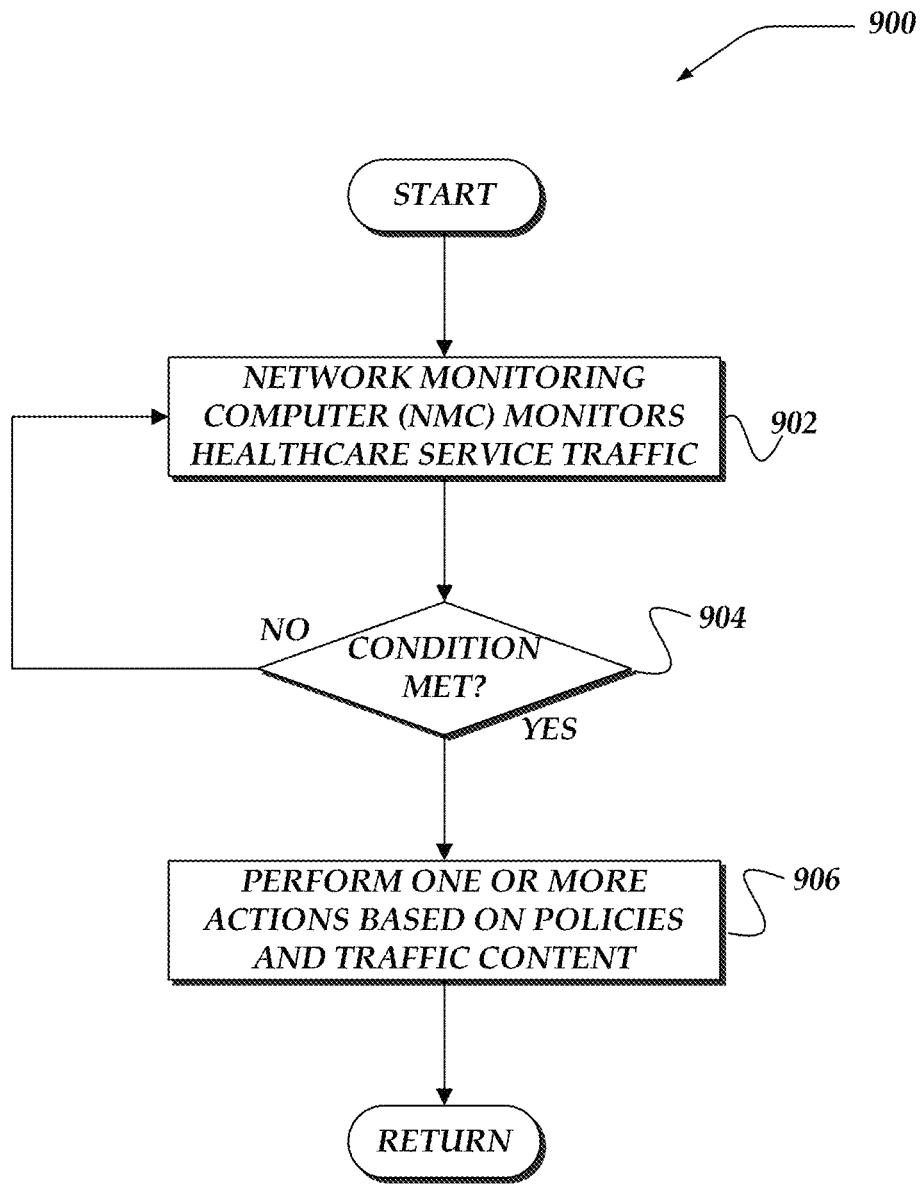
FIG. 9 illustrates an overview flowchart of a process for improving healthcare operations with passive network monitoring in accordance with at least one of the various embodiments.

FIG. 9 illustrates an overview flowchart of process 900 for improving healthcare operations with passive network monitoring in accordance with at least one of the various embodiments. After a start block, at block 902, in at least one of the various embodiments, a network monitoring computer (NMC) may be arranged to monitor healthcare service network traffic. As described above, in at least one of the various embodiments, some of the network traffic in a healthcare environment may use healthcare information protocols, such as, HL7, DICOM, or the like. Accordingly, the NMC may be arranged to identify and monitor such network traffic.

In at least one of the various embodiments, the NMC may be arranged to recognize various features of the healthcare traffic. For example, various segments, fields, or values, for HL7 traffic may be identified by the NMC from the monitored traffic. Likewise, in some embodiments, NMCs may be arranged to generate one or more metrics associated with information embedded in the healthcare traffic. For example, in some embodiments an NMC may be arranged to generate metrics for tracking the time it takes from when a patient checks-in to clinic until they check-out.

In at least one of the various embodiments, the particular monitoring configurations may be customized/targeted for each healthcare environment. In at least one of the various embodiments, the particular metrics that may be generated may depend on configuration information and/or policies being employed by the NMCs. Accordingly, in some embodiments, users may be enabled to provide configuration that is used to determine which metric to measure, conditions, subsequent actions, reports, or the like, or combination thereof. In some embodiments, configuration information (including rules, or policies) may be implemented using one or more well-known programming languages, such as, Javascript, TCL, Java, Perl, Python, or the like, or combination thereof. In some embodiments, the configuration information may be provided via a graphical user-interface, or the like, that enables configuration information to be generated without manual programming.

At decision block 904, in at least one of the various embodiments, if one or more conditions may be met, control may flow to block 906; otherwise, control may be loop back block 902. In at least one of the various embodiments, configuration information may define conditions using various logical or arithmetic expressions. In some cases, more than condition may be chained together into a single test. For example, in some embodiments, threshold values may be defined for various performance metrics, such that if a threshold value is exceeded the condition may be met.

At block 906, in at least one of the various embodiments, the NMC may perform one or more actions based on policies, conditions, the network traffic content, or the like. As described above, in some embodiments, one or more actions may be associated with the conditions. Accordingly, in at least one of the various embodiments, if the conditions are met, those associated actions may be performed. In some cases, the NMC may provide a notification to another system, server, or user that may perform the actions that are associated with conditions. Next, control may be returned to a calling process.

Figure 10:
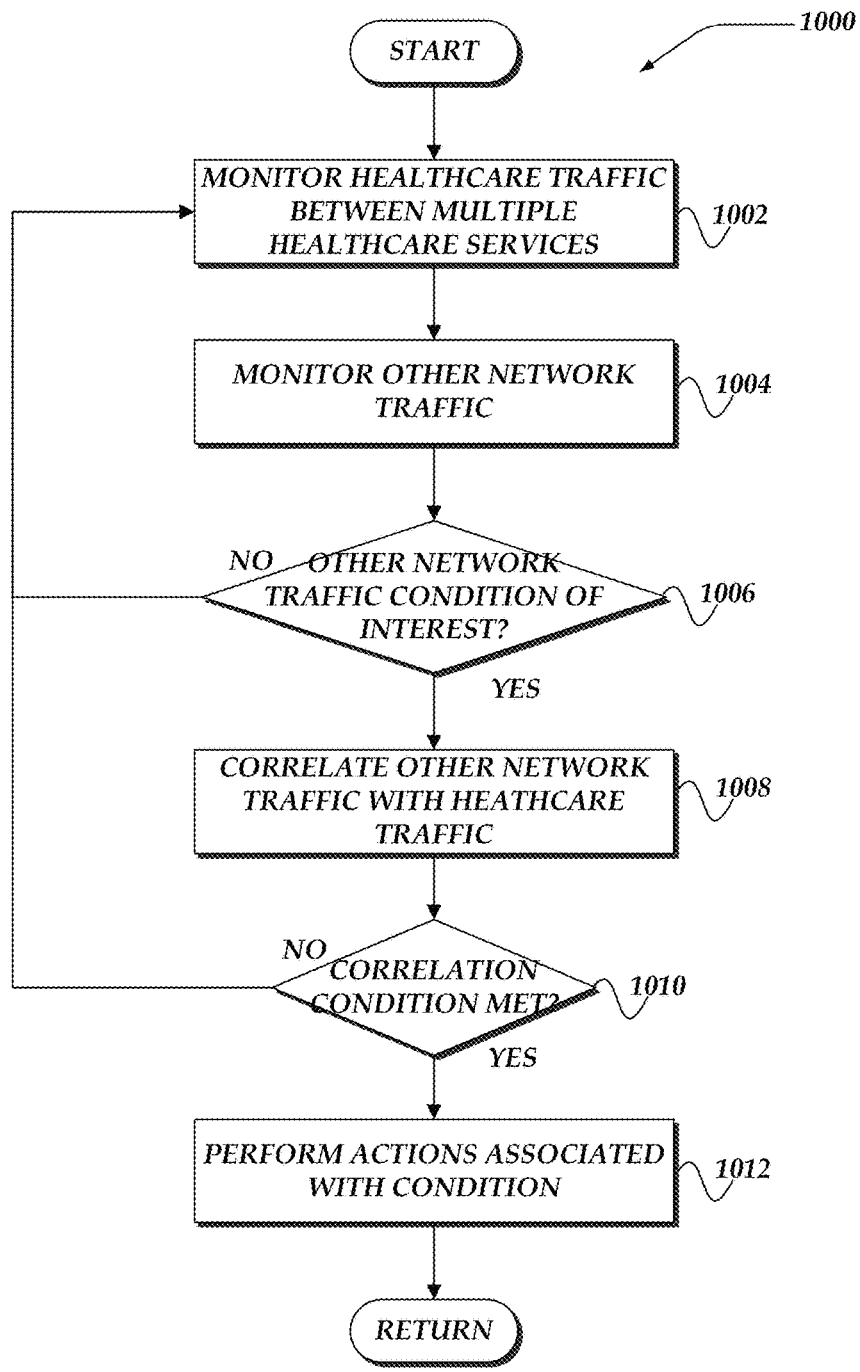
FIG. 10 illustrates an overview flowchart of a process for correlating healthcare traffic with other network traffic to improve healthcare operations in accordance with at least one of the various embodiments.

FIG. 10 illustrates an overview flowchart of process 1000 for correlating healthcare traffic with other network traffic to improve healthcare operations in accordance with at least one of the various embodiments. After a start block, at block 1002, in at least one of the various embodiments, healthcare traffic provided by one or more healthcare services may be monitored by a network monitoring computer (NMC). As described above, an NMC may be configured to monitor the contents of healthcare network traffic, such as, HL7 traffic. At block 1004, in at least one of the various embodiments, the NMC may be arranged to monitor other network traffic in the healthcare environment. In at least one of the various embodiments, the NMC is not limited to just monitor healthcare network traffic. In some embodiments, the NMC may be arranged to monitor other network traffic and/or protocols that are occurring on the networks. Accordingly, in at least one of the various embodiments, rules, or policies or other configuration information may control how the other network traffic may be monitored.

At decision block 1006, in at least one of the various embodiments, if the other network traffic produces a condition of interest, control may flow block 1008; otherwise, control may loop back to block 1002 to continue monitoring the network traffic. In at least one of the various embodiments, one or more rules, or policies may define conditions that indicate that something of interest has occurred in the other network traffic.

At block 1008, in at least one of the various embodiments, the other network traffic may be correlated with the healthcare traffic. In at least one of the various embodiments, the selected other network traffic may be correlated with healthcare traffic based on one or more rules, or policies. For example, one correlation may identify healthcare traffic that was directed to the same host as the other network traffic. Likewise, correlations may be defined as healthcare traffic that originated from the one or more hosts that sent the other network traffic.

At decision block 1010, in at least one of the various embodiments, if one or more correlation condition is met, control may flow to block 1012; otherwise, control may loop back to block 1002 to continue monitoring the network traffic. In one or more embodiments, policy, rules and/or configuration information may define one or more conditions to test with respect the correlation outcomes of the healthcare traffic and the other network traffic. In some embodiments, there may be multiple conditions that may be tested for more than one correlation outcome.

At block 1012, in at least one of the various embodiments, one or more actions associated with the conditions may be performed by the NMC. As described above, if the conditions are met there may be one or more actions performed as result. Actions may include communicating notifications, raising alarms, generating a log entry, updating a dashboard report that shows one or more metrics, or the like, or combination thereof.

In at least one of the various embodiments, the particular actions that are performed may be defined using configuration information, rules, or policies. Where the particular actions may be tailored to a particular conditions and operating environment. Next, control may be returned to a calling process.

In at least one of the various embodiments, real-time monitoring of network traffic by the NMC enable several applications that would be unavailable without cross-service monitoring. As described above, one or more healthcare services may be operating independent of each other, even though one or more outcomes in the healthcare environment may be dependent.

Also, in at least one of the various embodiments, since some healthcare services may employ incompatible and/or proprietary object models, data bases, or the like, direct interoperation may be difficult. Accordingly, since the healthcare services may use a standard healthcare messaging protocol, such as, HL7, to operate in the network, a separate NMC that is passively monitoring the network traffic may be able to capture the traffic and correlate events between otherwise independent/disparate healthcare services.

Further, in at least one of the various embodiments, network-wide monitoring of the healthcare traffic and network traffic enable the NMC to perform real-time auditing of the healthcare environment. As described above, if triggers are defined in configuration information, the NMC may perform various actions if the conditions associated with one or more of the triggers may be met.

In at least one of the various embodiments, the NMC may monitor real-time HL7 transactions and ensure that the contents of the message conform to organizational/regulatory requirements. For example, a NMC may be arranged confirm that the correct insurance codes are used for particular diagnosis in accordance with organizational rules. In at least one of the various embodiments, if inconsistent insurance codes, or the like, are used the NMC may generate a notification that asks a user to correct entry, or otherwise, resolve the inconsistency.

In at least one of the various embodiments, a NMC may be arranged monitor prescription orders that may be electronically entered. Accordingly, in some embodiments, the NMC may be arranged perform a drug interaction check for the patient, before the patient goes to a pharmacy to attempt to fill the order. For example, the NMC may be arranged to observe drugs as they are being prescribed and then lookup the patient's current drug history and perform the drug interaction check. In this example, the drug interaction check may occur early in the process (e.g., before the patient has left the facility). And, in this example, the NMC may have access to patient data that may be unavailable to an outside/third-party pharmacy.

In at least one of the various embodiments, the NMC may be arranged to perform content based de-duplication of healthcare communications by inspecting the contents of the messages. For example, healthcare service may be arranged to send messages more than once if the intended target is slow to acknowledge the message. Accordingly, while the follow-up healthcare messages may be unique as far as the underlying network protocols are concerned, they may be duplicate healthcare messages. Accordingly, the NMC may inspect the content of the healthcare message to determine if the message is a duplicate that may be discarded.

In at least one of the various embodiments, a NMC may be arranged to perform real-time monitoring of patient admissions. In some embodiments, each time a patient is admitted and/or checks-in into a healthcare facility, one or more healthcare message may be generated. An NMC that is arranged to passively monitor healthcare traffic may inspect the patient admission/check-in messages. Accordingly, in at least one of the various embodiments, one or more rules, or policies may be enforced, such as, identifying if the patient needs an interpreters and/or if one has been scheduled or otherwise available. In practice, a healthcare facility will probably have a workflow process in place that is intended to make sure patients that need interpreters have access to them. So in those cases, the NMC provides another layer of protection to ensure that an interpreter is available.

In at least one of the various embodiments, as described briefly above, the NMC may be arranged to passively monitor the network traffic of the healthcare facility. In the course of monitoring the network traffic the NMC may automatically detect the different healthcare services that are operating. In at least one of the various embodiments, the NMC may be arranged to determine the different healthcare services from the characteristics of the healthcare traffic. Also, the NMC may be arranged to identify/map-out the communication patterns of the different healthcare services. For example, the NMC may identify that a healthcare service may be communication with an outside service. The NMC may be arranged to maintain a list of authorized external services and detect if data is being communication with an unauthorized service.

Likewise, in some embodiments, disparate healthcare services may be configured to communication using a common/standard interface. In some cases, (e.g., HL7) there may be significant flexibility in how a standard interface is used. For example, different named fields may be used for the same information, depending on the interface is configured. Accordingly, in at least one of the various embodiments, the NMC may be configured to generate an interface map that describes how the disparate healthcare services may be using an interface. The dependencies between the different users of the interface may be identified. For example, if field X is used for value type Y by one or more healthcare service HL7 interfaces, using field Z for value type Y may cause communication problems. However, since the healthcare services are separate from each other, often with their own separate interface definition tools, it may be cumbersome to ensure that a consistent interface is maintained across services.

Accordingly, in at least one of the various embodiments, the NMC may be arranged to generate a map of the interface(s) as used in the healthcare computing environment. Also, in at least one of the various embodiments, the NMC may be arranged to identify healthcare services that are using inconsistent interface definitions.

Figure 11:
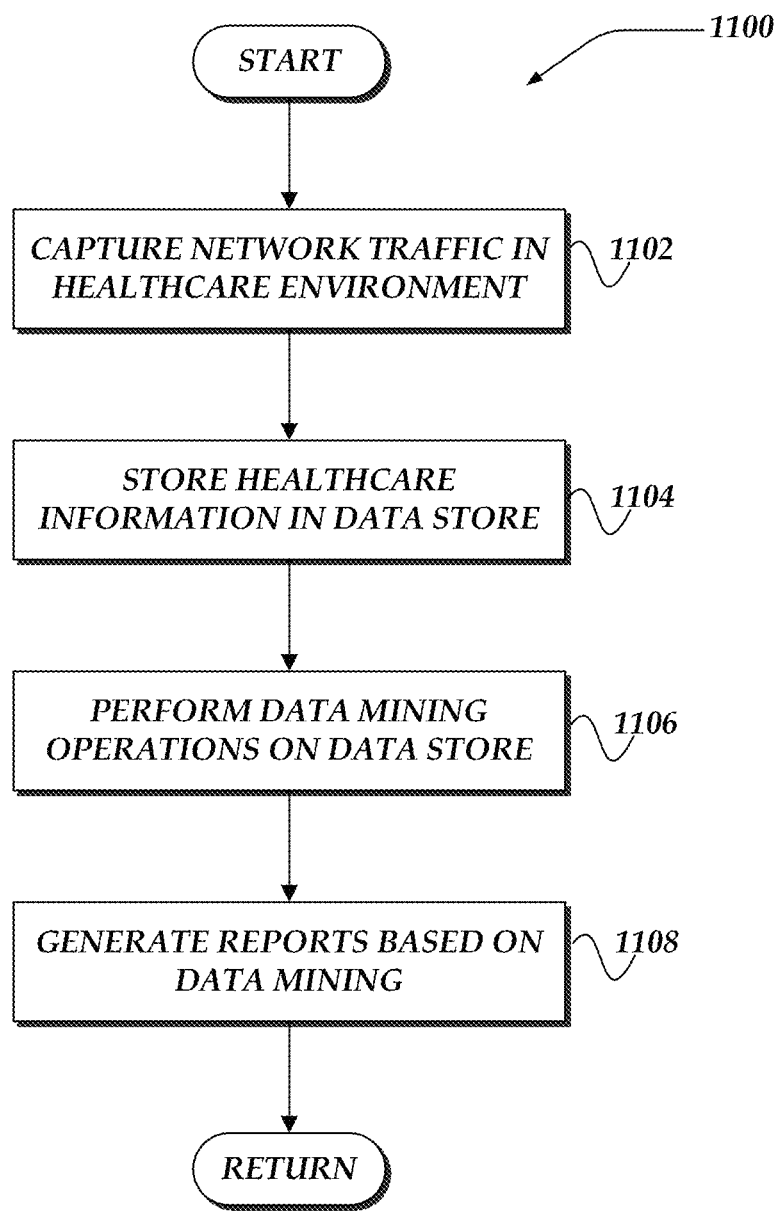
FIG. 11 illustrates an overview flowchart of a process for deferred non-real-time analysis of healthcare traffic to improve healthcare operations in accordance with at least one of the various embodiments.

FIG. 11 illustrates an overview flowchart of process 1100 for deferred non-real-time analysis of healthcare traffic to improve healthcare operations in accordance with at least one of the various embodiments. After a start block, at block 1102, in at least one of the various embodiments, network traffic occurring in the healthcare environment may be captured. In at least one of the various embodiments, some or all of the monitored healthcare traffic may be captured for archiving/storage, and analysis.

In at least one of the various embodiments, a network monitoring computer (NMC) may be arranged to selectively capture healthcare traffic for storage rather than simply monitoring the network traffic in real-time. In some embodiments, the traffic may be selected by the NMCs using one or more templates, filters, policies, or the like, or combination thereof. The healthcare traffic may be designated according to its source, origin, application, time-of-day, payload content (e.g., via pattern matching), tags, or the like, or combination thereof.

In at least one of the various embodiments, healthcare traffic may be allowed to continue to its normal destination as the NMC may be arranged to passively monitor the traffic without altering or interfering with it. Accordingly, in some embodiments, the captured data may be duplicated for storage while the originating network flow flows uninterrupted to its intended destination.

At block 1104, in at least one of the various embodiments, healthcare information derived from the captured network traffic may be stored as records in a data store. In at least one of the various embodiments, the NMC may be arranged to transform the captured healthcare traffic into records. In some embodiments, these records may be arranged to represent entities in the healthcare traffic as objects. Also, in at least one of the various embodiments, the records may combine one or more healthcare traffic packets into one or more records. For example, one or more message segments in a HL7 message may represent the personal details of a patient. Accordingly, a patient object may be generated that encapsulated the properties of patients that may be extracted from a HL7 message. Likewise, other entities, such as, lab reports, prescriptions, healthcare providers, diagnostic tools, clinics, schedules, diseases, or the like, or combination thereof, may be represented as objects In at least one of the various embodiments, the record information may be stored in a local or remote database that enables other computers to access the data without interfering with ongoing monitoring and/or capturing operations. In at least one of the various embodiments, the data store used for storing the records may be located and/or accessible within a cloud-based environment. In some embodiments, one or more highly-available/highly-redundant storage system may be used depending on the purpose and/or value of the stored records.

At block 1106, in at least one of the various embodiments, various data mining actions may be performed on the stored healthcare information. In at least one of the various embodiments, users may perform queries against the stored healthcare information. Also, in at least one of the various embodiments, one or more automated processes may query the storage information periodically. Also, in some embodiments, rules, or policies may be arranged to perform automated data mining queries and perform additional actions if necessary. For example, in some embodiments, an automated process may query the number of patients having a particular diagnosis that were admitted into a hospital. Accordingly if a threshold is exceeded, some additional actions may be taken. In some embodiments, the particular actions to be taken and the conditions/thresholds values may be defined in one or more rules, policies, configuration information, or the like, or combination thereof.

At block 1108, in at least one of the various embodiments, one or more reports may be generated based on the data mining. In at least one of the various embodiments, results of queries may be used to various reports, including, text reports, visualizations, or the like, or combination thereof. Next, control may be returned to a calling process.

In at least one of the various embodiments, healthcare records and the associated healthcare information may be analyzed (data mined) to discover insights about local operations of a healthcare that may be used to improve those operations. In at least one of the various embodiments, the records captured by the NMC may come for healthcare traffic and/or network traffic generated by separate healthcare services in the healthcare environment. Accordingly, such system may not otherwise be integrated with a centrally accessible data store that simultaneously stores operational information from disparate systems.

In at least one of the various embodiments, different healthcare services in a healthcare computing environment may use incompatible (e.g., proprietary) databases/data-descriptions for storing their own data/operation history. However, in some embodiments, they may be arranged to communicate with other healthcare services using a standard healthcare communication protocol, such as, HL7, or the like. Accordingly, the NMC may capture the information while it is a non-proprietary format. This may at least enable, traffic from otherwise incompatible services to be stored and correlated for later analysis.

In at least one of the various embodiments, stored records may be used to identify trends in reported diseases. Accordingly, reports may be generated that described historical trends in diagnosis of disease. In some embodiments, one or more threshold values may be defined that trigger notifications. For example, if disease of interest begins to be seen in patients more often, the system may provide an early indication that a particular disease may unexpectedly or uncharacteristically impacting one or more patient communities.

In some embodiments, healthcare traffic and/or records for one healthcare provider may be combined with other healthcare providers. Accordingly, data mining and/or analyses may incorporate data from multiple healthcare environments. Likewise, in some embodiments, anonymized healthcare records may be provided to the public and/or government agencies for additional data mining In at least one of the various embodiments, the healthcare records may be mined to determine correlations between otherwise separate healthcare services. In some embodiments, dependencies between services that otherwise appear to be independent may be determined and/or monitored. In some cases, the data mining may discover that one or more healthcare services are providing duplicate services.

In other cases, the cross-service data mining may discover two or more services are generating inconsistent or incompatible actions. For example, in some embodiments, one healthcare service may be coding a procedure using different codes than is expected. In this example, mismatched codes may result in over-charging or under-charging for services which could cause significant problems for the healthcare organization with respect its payer relationships, such as, problems with insurance companies, Medicare, Medicaid, or the like.

In at least one of the various embodiments, as described above, data mining cross-healthcare service information collected by the NMC may be enable one or more epidemiological reports that track/identify the rise of a disease. In some embodiments, real-time trends may be compared with values (threshold value) provided by data mining the historical records. Thus, in some embodiments, if a real-time trend exceeds a historical trend, the appropriate notifications/reports may be communicated.

In at least one of the various embodiments, patient safety initiatives may be supported by data mining of the stored healthcare records. Patient health may be correlated with employee activities, such as, shift changes, individual assignments, training level of on-duty staff, workload, time-of-data, or the like, or combination thereof. For example, healthcare records may be data mined to identify shifts that experience an increase in bad/poor patient outcomes. Likewise, for example, the causes or correlations to the bad outcomes that may be associated with those shifts may be determined.

In at least one of the various embodiments, prescriptions for drugs and treatments may be communicated within the healthcare network environment. Accordingly, a NMC may be arranged to monitor and store information related to prescriptions.

In at least one of the various embodiments, the data store may enable data mining to determine the source/destination of various prescriptions, patient information, provider information, or the like. For example, the data store may be mined to determine if there are unexpected dependencies, such as: if certain drugs are more likely to prescribe after hours; determining variances in the types of drugs that may be prescribed for the same diagnosis/disease/treatment; variations in historical trends for particular drugs; same drugs being prescribed twice by different providers/departments/clinic; variances/trends in dosage; or the like.

In at least one of the various embodiments, data mining of the healthcare records may enable monitoring of patient admission and discharge. For example, an HL7 message that reports that a patient had checked in may be captured and another HL7 message may be captured if the patient is discharged. In some cases, the healthcare service that checks-in the patient may not be that same one that discharges the patient. Accordingly, by correlating the check-in message from one healthcare service with the discharge message from another healthcare service, the NMC may enable improved recording keeping and patient load trends which may be useful for proactively setting staffing levels, or the like. Similarly, in at least one of the various embodiments, the healthcare records may be used for tracking re-admission trends.

Further, in at least one of the various embodiments, the healthcare records may be used to track referral practices and generate referral trends. For example, if a patient is referred to a specialist, a corresponding HL7 message may generated. Likewise, in some embodiments, treatment activity by the specialist may be tracked and correlated with the referrals.

In at least one of the various embodiments, one or more reports for tracking/describing a patient's visit to a healthcare facility may be generated from the healthcare records. In some embodiments, an NMC may be arranged to monitor and capture healthcare messages that may be associated with the patient's visit. Accordingly, in some embodiments, a report may be generated that illustrates each event that involving the patient while they were receiving treatment at the healthcare facility. For example, a report may show a patient going from admission, to a consult with a doctor, to radiology, to the pharmacy, and so on. In some embodiments, information captured from the healthcare traffic may enable each event experienced by the patient to be described, along with time/date information, wait-times, durations, provider identifiers, activities, annotations, or the like. Such a report may enable comparing how different patients may access the various services/resources in the healthcare facility. In some embodiments, these reports may help identify bottlenecks in a hospital workflow. Accordingly, in this example, by modifying the routing/scheduling of patients bottlenecks may be reduced. It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multiprocessor computer system. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware based systems, which perform the specified actions or steps, or combinations of special purpose hardware and computer instructions. The foregoing example should not be construed as limiting and/or exhaustive, but rather, an illustrative use case to show an implementation of at least one of the various embodiments of the invention.

Further, in one or more embodiments (not shown in the figures), the logic in the illustrative flowcharts may be executed using an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. In at least one embodiment, a microcontroller may be arranged to directly execute its own embedded logic to perform actions and access its own internal memory and its own external Input and Output Interfaces (e.g., hardware pins and/or wireless transceivers) to perform actions, such as System On a Chip (SOC), or the like.

What is claimed as new and desired to be protected by Letters Patent of the United States is:

1. A method for monitoring flows of packets over a network, wherein one or more processors in a network computer execute instructions to perform actions, comprising:
   instantiating a network monitoring application to perform actions based on one or more healthcare traffic flows provided by one or more healthcare services including:
   employing the one or more processors to select one or more types of a plurality of healthcare messages based on configuration information that includes one or more of a filter, a rule, or a condition;

employing the one or more processors to monitor content of the selected type of the plurality of healthcare messages in the one or more healthcare protocol traffic flows, wherein each healthcare message includes a data structure that includes a plurality of different types of healthcare segments that have one or more fields, wherein a particular format of the data structure for each healthcare message is based on one or more of an implementation of a corresponding messaging system or a version of a corresponding healthcare protocol traffic flow;

employing the one or more processors to determine one or more healthcare values from the one or more fields of the one or more healthcare segments based on the particular data structure format of each healthcare message;

employing the one or more processors to determine one or more values from one or more other traffic flows that include a plurality of messages that employ a protocol different from the one or more healthcare protocol traffic flows;

employing the one or more processors to compare one or more patterns in the one or more healthcare traffic flows to identify each of the healthcare services that are communicating over a network and correlate one or more of context or relationship between the one or more identified healthcare services, wherein the correlation is employed in identifying each health care service that is inadvertently sharing information with one or more other healthcare services, or identifying each healthcare service that is failing to share information with the one or more other healthcare services, and wherein the comparison of patterns in healthcare traffic flows to identify health care services improves correlation of the one or more of contexts or relationships for otherwise incompatible healthcare services;

employing the one or more processors to compare one or more health care values to the one or more determined values from the other traffic flows to determine a failure to follow one or more conditions of a policy, one or more other actions to be scheduled in accordance with the policy, and meeting the one or more conditions of the policy, wherein the one or more conditions include one or more of a threshold value for a performance metric; and employing the comparison of the one or more healthcare values and the one or more determined values from the other traffic flows that meets the one or more conditions of the policy, or provides conclusions for two or more health care services to use the one or more processors to perform one or more other actions with one or more rules, wherein a result of the one or more other actions is communicated to one or more other network computers.

2. The method of claim 1, wherein the healthcare protocol traffic is compliant with one or more of Health Level Seven (HL7) standard, or Digital Imaging and Communications in Medicine (DICOM) standard.

3. The method of claim 1, further comprising employing the one or more processors to perform further actions, including:

providing one or more other healthcare values from one or more other healthcare protocol traffic flows provided by the one or more other healthcare services; and employing a comparison of the one or more healthcare values and the one or more other healthcare values that meet the one or more conditions to perform one or more other actions with one or more rules, wherein a result of the one or more other actions is communicated to one or more other network computers.

4. The method of claim 1, further comprising employing the one or more processors to perform further actions, including:

providing one or more records that include a portion of the content of the plurality of healthcare messages in the one or more healthcare protocol traffic flows and the one or more healthcare values;

storing the one or more records in a data store; and providing one or more reports using one or more queries and the one or more records.

5. The method of claim 1, wherein the one or more actions include:

providing one or more patient values from the one or more healthcare protocol traffic flows from the one or more healthcare services; and providing trend information based on the one or more patient values and associated with one or more of a disease, a diagnosis, a payment, patient schedules, provider schedules, lab results, or, a duration of patient visits.

6. The method of claim 1, wherein the one or more conditions, include, comparing the one or more healthcare values in real-time with one or more defined values.

7. The method of claim 1, wherein the one or more conditions, include, comparing one or more healthcare transaction results in real-time with one or more defined values, wherein one or more incomplete healthcare transactions may be identified.

8. The method of claim 1, wherein the one or more actions include, providing a notification when a drug prescribed to a patient is negatively impacted by another drug prescribed to the patient.

9. A system for monitoring flows of packets over a network comprising:

a network computer, comprising:

a transceiver that communicates over the network;

a memory that stores at least instructions; and one or more processors that execute instructions that perform actions, including:

instantiating a network monitoring application to perform actions based on one or more healthcare traffic flows provided by one or more healthcare services including:

employing the one or more processors to select one or more types of a plurality of healthcare messages based on configuration information that includes one or more of a filter, a rule, or a condition;

employing the one or more processors to monitor content of the selected type of the plurality of healthcare messages in the one or more healthcare protocol traffic flows, wherein each healthcare message includes a data structure that includes a plurality of different types of healthcare segments that have one or more fields, wherein a particular format of the data structure for each healthcare message is based on one or more of an implementation of a corresponding messaging system or a version of a corresponding healthcare protocol traffic flow;

employing the one or more processors to determine one or more healthcare values from the one or more fields of the one or more healthcare segments based on the particular data structure format of each healthcare message;

employing the one or more processors to determine one or more values from one or more other traffic flows that include a plurality of messages that employ a protocol different from the one or more healthcare protocol traffic flows;

employing the one or more processors to compare one or more patterns in the one or more healthcare traffic flows to identify each of the healthcare services that are communicating over a network and correlate one or more of context or relationship between the one or more identified healthcare services, wherein the correlation is employed in identifying each health care service that is inadvertently sharing information with one or more other healthcare services, or identifying each healthcare service that is failing to share information with the one or more other healthcare services, and wherein the comparison of patterns in healthcare traffic flows to identify health care services improves correlation of the one or more of contexts or relationships for otherwise incompatible healthcare services;

employing the one or more processors to compare one or more health care values to the one or more determined values from the other traffic flows to determine a failure to follow one or more conditions of a policy, one or more other actions to be scheduled in accordance with the policy, and meeting the one or more conditions of the policy, wherein the one or more conditions include one or more of a threshold value for a performance metric; and employing the comparison of the one or more healthcare values and the one or more determined values from the other traffic flows that meets the one or more conditions of the policy, or provides conclusions for two or more health care services to use the one or more processors to perform one or more other actions with one or more rules, wherein a result of the one or more other actions is communicated to one or more other network computers; and a client computer, comprising:
a transceiver that communicates over the network;
a memory that stores at least instructions; and
one or more processors that execute instructions that perform actions, including:
visualizing one or more reports made from the result of the one or more other actions.

10. The system of claim 9, wherein the healthcare protocol traffic is compliant with one or more of Health Level Seven (HL7) standard, or Digital Imaging and Communications in Medicine (DICOM) standard.

11. The system of claim 9, wherein the one or more processors of the network computer execute instructions that perform actions, further comprising:
providing one or more other healthcare values from one or more other healthcare protocol traffic flows provided by the one or more other healthcare services; and
employing a comparison of the one or more healthcare values and the one or more other healthcare values that meet the one or more conditions to perform one or more other actions with one or more rules, wherein a result of the one or more other actions is communicated to one or more other network computers.

12. The system of claim 9, wherein the one or more processors of the network computer execute instructions that perform actions, further comprising:
providing one or more records that include a portion of the content of the plurality of healthcare messages in the one or more healthcare protocol traffic flows and the one or more healthcare values;
storing the one or more records in a data store; and
providing one or more reports using one or more queries and the one or more records.

13. The system of claim 9, wherein the one or more actions include:
providing one or more patient values from the one or more healthcare protocol traffic flows from the one or more healthcare services; and
providing trend information based on the one or more patient values and associated with one or more of a disease, a diagnosis, a payment, patient schedules, provider schedules, lab results, or, a duration of patient visits.

14. The system of claim 9, wherein the one or more conditions, include, comparing the one or more healthcare values in real-time with one or more defined values.

15. The system of claim 9, wherein the one or more conditions, include, comparing one or more healthcare transaction results in real-time with one or more defined values, wherein one or more incomplete healthcare transactions may be identified.

16. The system of claim 9, wherein the one or more actions include, providing a notification when a drug prescribed to a patient is negatively impacted by another drug prescribed to the patient.

17. A processor readable non-transitory storage media that includes instructions for monitoring flows of packets over a network, wherein execution of the instructions by one or more hardware processors performs actions, comprising:
instantiating a network monitoring application to perform actions based on one or more healthcare traffic flows provided by one or more healthcare services including:
employing the one or more processors to select one or more types of a plurality of healthcare messages based on configuration information that includes one or more of a filter, a rule, or a condition;
employing the one or more processors to monitor content of the selected type of the plurality of healthcare messages in the one or more healthcare protocol traffic flows, wherein each healthcare message includes a data structure that includes a plurality of different types of healthcare segments that have one or more fields, wherein a particular format of the data structure for each healthcare message is based on one or more of an implementation of a corresponding messaging system or a version of a corresponding healthcare protocol traffic flow;
employing the one or more processors to determine one or more healthcare values from the one or more fields of the one or more healthcare segments based on the particular data structure format of each healthcare message;
employing the one or more processors to determine one or more values from one or more other traffic flows that include a plurality of messages that employ a protocol different from the one or more healthcare protocol traffic flows;
employing the one or more processors to compare one or more patterns in the one or more healthcare traffic flows to identify each of the healthcare services that are communicating over a network and correlate one or more of context or relationship between the one or more identified healthcare services, wherein the correlation is employed in identifying each health care service that is inadvertently sharing information with one or more other healthcare services, or identifying each healthcare service that is failing to share information with the one or more other healthcare services, and wherein the comparison of patterns in healthcare traffic flows to identify health care services improves correlation of the one or more of contexts or relationships for otherwise incompatible healthcare services;

employing the one or more processors to compare one or more health care values to the one or more determined values from the other traffic flows to determine a failure to follow one or more conditions of a policy, one or more other actions to be scheduled in accordance with the policy, and meeting the one or more conditions of the policy, wherein the one or more conditions include one or more of a threshold value for a performance metric; and employing the comparison of the one or more healthcare values and the one or more determined values from the other traffic flows that meets the one or more conditions of the policy, or provides conclusions for two or more health care services to use the one or more processors to perform one or more other actions with one or more rules, wherein a result of the one or more other actions is communicated to one or more other network computers.

18. The media of claim 17, wherein the healthcare protocol traffic is compliant with one or more of Health Level Seven (HL7) standard, or Digital Imaging and Communications in Medicine (DICOM) standard.

19. The media of claim 17, further comprising employing the one or more processors to perform further actions:

providing one or more other healthcare values from one or more other healthcare protocol traffic flows provided by the one or more other healthcare services; and employing a comparison of the one or more healthcare values and the one or more other healthcare values that meet the one or more conditions to perform one or more other actions with one or more rules, wherein a result of the one or more other actions is communicated to one or more other network computers.

20. The media of claim 17, further comprising employing the one or more hardware processors to perform further actions:

providing one or more records that include a portion of content of the one or more healthcare protocol traffic flows and the one or more healthcare values;

storing the one or more records in a data store; and providing one or more reports using one or more queries and the one or more records.

21. The media of claim 17, wherein the one or more actions include:

providing one or more patient values from the one or more healthcare protocol traffic flows from the one or more healthcare services; and providing trend information based on the one or more patient values and associated with one or more of a disease, a diagnosis, a payment, patient schedules, provider schedules, lab results, or, a duration of patient visits.

22. The media of claim 17, wherein the one or more conditions, include, comparing the one or more healthcare values in real-time with one or more defined values.

23. The media of claim 17, wherein the one or more conditions, include, comparing one or more healthcare transaction results in real-time with one or more defined values, wherein one or more incomplete healthcare transactions may be identified.

24. A network computer for monitoring flows of packets over a network, comprising:

a transceiver that communicates over the network;

a memory that stores at least instructions; and one or more processors that execute instructions that perform actions, including:

instantiating a network monitoring application to perform actions based on one or more healthcare traffic flows provided by one or more healthcare services including:

employing the one or more processors to select one or more types of a plurality of healthcare messages based on configuration information that includes one or more of a filter, a rule, or a condition;

employing the one or more processors to monitor content of the selected type of the plurality of healthcare messages in the one or more healthcare protocol traffic flows, wherein each healthcare message includes a data structure that includes a plurality of different types of healthcare segments that have one or more fields, wherein a particular format of the data structure for each healthcare message is based on one or more of an implementation of a corresponding messaging system or a version of a corresponding healthcare protocol traffic flow;

employing the one or more processors to determine one or more healthcare values from the one or more fields of the one or more healthcare segments based on the particular data structure format of each healthcare message;

employing the one or more processors to determine one or more values from one or more other traffic flows that include a plurality of messages that employ a protocol different from the one or more healthcare protocol traffic flows;

employing the one or more processors to compare one or more patterns in the one or more healthcare traffic flows to identify each of the healthcare services that are communicating over a network and correlate one or more of context or relationship between the one or more identified healthcare services, wherein the correlation is employed in identifying each health care service that is inadvertently sharing information with one or more other healthcare services, or identifying each healthcare service that is failing to share information with the one or more other healthcare services, and wherein the comparison of patterns in healthcare traffic flows to identify health care services improves correlation of the one or more of contexts or relationships for otherwise incompatible healthcare services;

employing the one or more processors to compare one or more health care values to the one or more determined values from the other traffic flows to determine a failure to follow one or more conditions of a policy, one or more other actions to be scheduled in accordance with the policy, and meeting the one or more conditions of the policy, wherein the one or more conditions include one or more of a threshold value for a performance metric; and employing the comparison of the one or more healthcare values and the one or more determined values from the other traffic flows that meets the one or more conditions of the policy, or provides conclusions for two or more health care services to use the one or more processors to perform one or more other actions with one or more rules, wherein a result of the one or more other actions is communicated to one or more other network computers.

25. The network computer of claim 24, wherein the healthcare protocol traffic is compliant with one or more of Health Level Seven (HL7) standard, or Digital Imaging and Communications in Medicine (DICOM) standard.

26. The network computer of claim 24, further comprising employing the one or more processors to perform further actions:
   providing one or more other healthcare values from one or more other healthcare protocol traffic flows provided by the one or more other healthcare services; and
   employing a comparison of the one or more healthcare values and the one or more other healthcare values that meet the one or more conditions to perform one or more other actions with one or more rules, wherein a result of the one or more other actions is communicated to one or more other network computers.

27. The network computer of claim 24, further comprising employing the one or more processors to perform further actions:
   providing one or more records that include a portion of content of the one or more healthcare protocol traffic flows and the one or more healthcare values;
   storing the one or more records in a data store; and
   providing one or more reports using one or more queries and the one or more records.

28. The network computer of claim 24, wherein the one or more actions include:
   providing one or more patient values from the one or more healthcare protocol traffic flows from the one or more healthcare services; and
   providing trend information based on the one or more patient values and associated with one or more of a disease, a diagnosis, a payment, patient schedules, provider schedules, lab results, or, a duration of patient visits.

29. The network computer of claim 24, wherein the one or more conditions, include, comparing the one or more healthcare values in real-time with one or more defined values.

30. The network computer of claim 24, wherein the one or more conditions, include, comparing one or more healthcare transaction results in real-time with one or more defined values, wherein one or more incomplete healthcare transactions may be identified.

* * * * *